United States Patent
Fey et al.

(10) Patent No.: US 12,172,996 B2
(45) Date of Patent: *Dec. 24, 2024

(54) METHYL {4,6-DIAMINO-2-[5-FLUORO-1-(2-FLUOROBENZYL)-1H-PYRAZOLO[3,4-B]PYRIDIN-3-YL]PYRIMIDIN-5-YL} CARBAMATE ACTIVE COMPOUND PRODUCT HAVING IMPROVED PROPERTIES, PRODUCTION AND FORMULATION THEREOF

(71) Applicant: Adverio Pharma GmbH, Leverkusen (DE)

(72) Inventors: Peter Fey, Wuppertal (DE); Michal Sowa, Wuppertal (DE); Joerg Brockob, Leverkusen (DE); Markus Longerich, Cologne (DE); Guido Becker, Krefeld (DE); Heike Neumann, Wuppertal (DE)

(73) Assignee: Adverio Pharma GmbH, Leverkusen (DE)

( * ) Notice: Subject to any disclaimer, the term of this patent is extended or adjusted under 35 U.S.C. 154(b) by 800 days.

This patent is subject to a terminal disclaimer.

(21) Appl. No.: 17/414,658

(22) PCT Filed: Dec. 16, 2019

(86) PCT No.: PCT/EP2019/085255
§ 371 (c)(1),
(2) Date: Jun. 16, 2021

(87) PCT Pub. No.: WO2020/126983
PCT Pub. Date: Jun. 25, 2020

(65) Prior Publication Data
US 2022/0048907 A1   Feb. 17, 2022

(30) Foreign Application Priority Data
Dec. 17, 2018 (EP) .................... 18213115

(51) Int. Cl.
C07D 471/04  (2006.01)

(52) U.S. Cl.
CPC ........ *C07D 471/04* (2013.01); *C07B 2200/13* (2013.01)

(58) Field of Classification Search
CPC ...... C07D 471/04; C07B 2200/13; A61P 9/00
See application file for complete search history.

(56) References Cited

U.S. PATENT DOCUMENTS

| | | |
|---|---|---|
| 5,994,538 A | 11/1999 | Carencotte et al. |
| 2012/0022084 A1 | 1/2012 | Follmann et al. |
| 2013/0143900 A1 | 6/2013 | Fey |
| 2016/0083416 A1 | 3/2016 | Poirier et al. |
| 2023/0067593 A1* | 3/2023 | Kersten ............... A61K 47/10 |
| 2023/0219952 A1* | 7/2023 | Fey .................... C07D 295/067 |
| | | 544/328 |

FOREIGN PATENT DOCUMENTS

| | | | |
|---|---|---|---|
| WO | 2000006569 A1 | 2/2000 | |
| WO | 2011064156 A2 | 6/2011 | |
| WO | 2011064171 A2 | 6/2011 | |
| WO | 2011147809 A1 | 12/2011 | |
| WO | 2013076168 A1 | 5/2013 | |
| WO | WO-2014128109 A1 * | 8/2014 | ........... A61K 31/519 |
| WO | WO-2016113415 A1 * | 7/2016 | |
| WO | WO-2017025981 A1 * | 2/2017 | ........... C07D 471/04 |
| WO | 2020126983 A1 | 6/2020 | |
| WO | 2020152010 A1 | 7/2020 | |

OTHER PUBLICATIONS

Fey, P. WO 2013/076168. English Translation. (Year: 2013).*
Byrn, S., et al., "Pharmaceutical Solids: A Strategic Approach to Regulatory Considerations", Pharmaceutical Research, 1995, 12(7):945-954.
Caira, M.R., "Crystalline Polymorphism of Organic Compounds", Topics in Current Chemistry, 1998, vol. 198, pp. 163-208, Springer Verlag, Berlin Heidelberg.
Kukes, V.G., ed., "Chapter 11.2 Relationship between a crystalline structure of a substance, pharmacokinetics and an efficacy of a drug", in Clinical Pharmacokinetics: Theoretical, Applied and Analytical Aspects, 2009, pp. 235-248.
International Search Report and Written Opinion from PCT/EP2021/066019, mailed Nov. 4, 2021, 22 pages.

* cited by examiner

*Primary Examiner* — Eric Olson
*Assistant Examiner* — Samuel L Galster

(57) ABSTRACT

The present invention relates to methyl {4,6-diamino-2-[5-fluoro-1-(2-fluorobenzyl)-1H-pyrazolo[3,4-b]pyridin-3-yl]pyrimidin-5-yl}carbamate in the form of a novel active compound product having improved properties, for example in respect of the isolability of the active compound product, the dischargeability of the active compound product after isolation and drying and also conveyability, sieveability and micronizability of the active compound product, and to processes for the production and formulation thereof.

13 Claims, 3 Drawing Sheets

Figure 1:
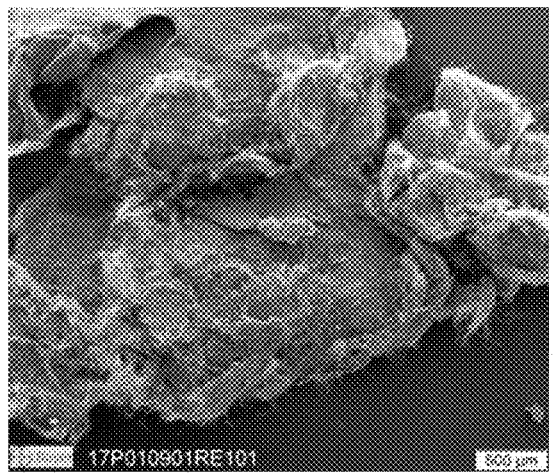

METHYL {4,6-DIAMINO-2-[5-FLUORO-1-(2-FLUOROBENZYL)-1H-PYRAZOLO[3,4-B]PYRIDIN-3-YL]PYRIMIDIN-5-YL} CARBAMATE ACTIVE COMPOUND PRODUCT HAVING IMPROVED PROPERTIES, PRODUCTION AND FORMULATION THEREOF

This application is a national stage entry under 35 U.S.C. § 371 for International Application No. PCT/EP2019/085255, filed on Dec. 16, 2019, the contents of which are incorporated herein by reference in its entirety, which claims priority to European Patent Application No. 18213115.1, filed on Dec. 17, 2018.

The present invention relates to a novel methyl {4,6-diamino-2-[5-fluoro-1-(2-fluorobenzyl)-1H-pyrazolo[3,4-b]pyridin-3-yl]pyrimidin-5-yl}carbamate active compound product having improved properties, for example in respect of the isolability of the active compound product, the dischargeability of the active compound product after isolation and drying and also conveyability, sieveability and micronizability of the active compound product, and to processes for the production and formulation of a dosage form thereof.

There are many factors influencing the suitability of an active compound product for producing pharmaceutical dosage forms. Essential for the production of pharmaceutical dosage forms on an industrial scale in particular are for example a good isolability of the active compound product, a good dischargeability of the active compound product after isolation and drying and also conveyability, sieveability and micronizability of the active compound product. These may be influenced for example by the solid-state properties of the active compound product such as shape and size. Known techniques for producing readily processable pharmaceutical active compound products are particle size-reducing processes such as micronization using jet mills or else wet milling, or particle size-increasing processes such as for example agglomeration processes.

A further essential solid-state property is the presence of a defined modification of the active compound. The presence of the compound of formula (I) in the crystalline form of modification I is preferred.

In the context of the present invention, "compound of formula (I) in the crystalline form of modification I" is to be understood as meaning the modification of the compound of formula (I) which is defined as the crystalline form of modification I in WO 2013/076168; for example by reference to the x-ray diffractogram having defined peak maxima of the 2 theta angle at 5.9, 6.9 and 22.7 or at 5.9, 6.9, 16.2, 16.5, 24.1, 22.7 and 24.7; or via the IR spectrum having defined band maxima at 1707, 1633 and 1475 cm$^{-1}$ or at 1707, 1633, 1566, 1475, 1255 and 1223 cm$^{-1}$; or with the aid of the melting point of 257° C.

The solid-state properties of a pharmaceutical active compound have a decisive influence on the development of a dosage form and on the activity of the active compound in vivo.

Methyl {4,6-diamino-2-[5-fluoro-1-(2-fluorobenzyl)-1H-pyrazolo[3,4-b]pyridin-3-yl]pyrimidin-5-yl}carbamate of formula (I)

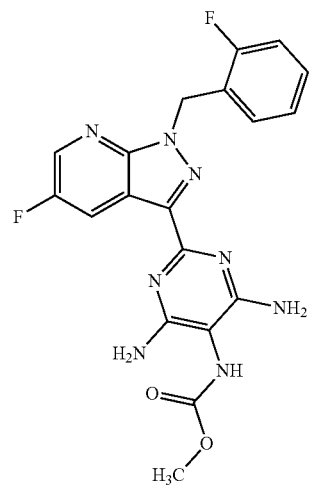

is a pharmaceutical active compound used for the treatment and/or prophylaxis of cardiovascular diseases. The synthesis of the compound of formula (I) is described in WO 2011/147809 and in WO 2013/076168. WO 2013/076168 describes inter alia the production of the compound of formula (I) in the crystalline form of the modifications I-V (polymorphs) and of various solvates.

WO 2013/076168 describes in example 13, method E or F, processes for producing the compound of formula (I) in crystalline form from the didimethylsulfoxide solvate of the compound of formula (I):

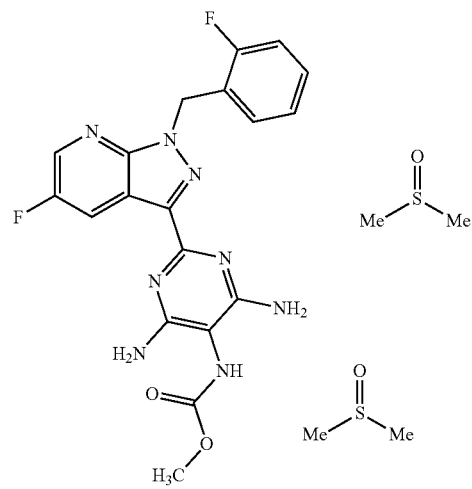

WO 2013/076168, Example 13, Method E:

2.0 g of the didimethyl sulfoxide solvate (produced according to example 13, method A in WO 2013/076168) were stirred at reflux temperature in 40 ml of ethyl acetate and 11.1 ml of ethanol for 17 h, cooled to RT and stirred for a further 1 h. The solid was filtered off under reduced pressure, washed four times with 1.4 ml of ethyl acetate in each case and dried under a light nitrogen stream in a vacuum drying cabinet at 50° C. This afforded 1.4 g of the title compound (compound of formula (I)) present in the crystalline form of modification I.

WO 2013/076168, Example 13, Method F:

0.5 g of the didimethyl sulfoxide solvate (produced according to example 13, method A in WO 2013/076168) were stirred at reflux temperature in 12.5 ml of solvent for 17 h, cooled to RT and stirred for a further 1 h. The solid was filtered off under reduced pressure, washed with 2 ml of solvent and dried under reduced pressure for 30 min. This afforded 0.3 g of the title compound present in the crystalline form of modification I.

The following solvents were used: 1.) 9 ml of ethyl acetate/3.5 ml of ethanol/0.3 ml of water; 2.) 12.5 ml of isopropanol; 3.) 12.5 ml of isopropanol/0.3 ml of water; 4.) 12.5 ml of methanol; 5.) 12.5 ml of methanol/0.3 ml of water; 6.) 12.5 ml of acetonitrile; 7.) 12.5 ml of acetone; 8.) 12.5 ml of tetrahydrofuran; 9.) 12.5 ml of methyl tert-butyl ether.

The production of the compound of formula (I) in the crystalline form of modification I as described in WO 2013/076168 results in a very slim, hair-like habit which on isolation by differential pressure filtration or else in filter centrifuges generates a very dense, felt-like filtercake having a very high tear strength due to the omnidirectional layering of the crystals. This effect can be expected to be more pronounced in a centrifugal field than in differential pressure filtration on account of the more compact configuration of the filtercake. This results in lengthy isolation times and during discharging from industrial isolation assemblies can cause problems where the filtercake does not fracture or break and thus blocks the discharge path. These felt-like filtercake structures can be expected to result in problematic bulk material behaviour in all subsequent process steps such as drying in a vacuum contact dryer, sieving or micronizing. Due to frequent sieve blockage, sieving on an industrial sieving machine may be carried out only at very low throughput and is therefore problematic. Solids conveying upstream of the subsequent micronization is difficult due to high electrostatic charge and associated adhesion to plant parts (for example conveying channel).

The present invention accordingly has for its object to produce an active compound product of the compound of formula (I) which compared to the active compound product produced with the process described in WO 2013/076168 (route 1) exhibits better properties inter alia in respect of the isolability of the active compound product, the dischargeability of the active compound product after isolation and drying and also conveyability, sieveability and micronizability, and is therefore suitable for industrial scale production of pharmaceutical active compounds in a solid dosage form. It is a further object of the present invention to produce the active compound of formula (I) in a defined modification, in particular in the crystalline form of modification I. It is a further object of the present invention to prevent the formation of hydrates or dihydrates of the active compound product of formula (I) during the production process according to the invention. In addition, compared to a solid dosage form which contains the active compound product of the compound of formula (I) produced with the process described in WO 2013/076168 (route 1) in the crystalline form of modification I, the active compound product produced by the process according to the invention in the solid dosage form produced therefrom shall show pharmaceutical properties which are at least equally good.

In the context of the present invention the term "active compound product of the compound of formula (I)" is used synonymously with the term "active compound product (I)" and likewise synonymously with the term "active compound product".

In the context of the present invention, "active compound product of the compound of formula (I) produced by route 1" or synonymously "active compound product (I)/active compound product produced by route 1" is defined as the active compound product of the compound of formula (I) produced by the process described in WO 2013/076168.

In the context of the present invention, "active compound product of the compound of formula (I) produced by route 2" or synonymously "active compound product (I)/active compound product produced by route 2" or synonymously "active compound product of the compound of formula (I) produced by the process according to the invention" or synonymously "inventive active compound product of the compound of formula (I)" is defined as the active compound product of the compound of formula (I) produced by the process according to the invention.

Both the "active compound product of the compound of formula (I) produced by route 1" and the "active compound product of the compound of formula (I) produced by route 2" comprise the compound of the formula (I) preferably in the crystalline form of modification I.

In the context of the present invention, "improved properties" for example in respect of the isolability of the active compound product, the dischargeability of the active compound product after isolation and drying and also conveyability, sieveability and micronizability are defined as an improvement in the recited properties of the active compound product produced by the inventive process of route 2 compared to the properties of the active compound product produced by the process of route 1. These "improved properties" are described by way of example in the present invention.

The prior art describes various processes for producing spherical agglomerates. U.S. Pat. No. 5,994,538 relates to spherical agglomerates of 10-phenothiazinylpropanoic acid and production thereof. The process for producing spherical agglomerates of 10-phenothiazinylpropanoic acid is characterized in that it comprises stirring a suspension of 10-phenothiazinylpropanoic acid in water in the presence of a water-immiscible agglomeration liquid (bridging liquid) selected from esters of aliphatic or cycloaliphatic acids, aliphatic or cycloaliphatic alcohols and aliphatic or cycloaliphatic ketones.

US2016083416 relates to a process for producing microsize abirateron acetate using spherical agglomeration that is said to afford high yields and is producible under conditions said to be more advantageous for industrial application. What is described is a process for producing microsize abirateron acetate in which the active compound is initially precipitated out of a solution in the form of thin crystals, these crystals are then agglomerated to isolate them from the reaction batch and the crystal agglomerates are finally deagglomerated by careful milling to obtain particles having the desired particle size distribution. Described as a decisive step is a system of three solvents where the active compound is initially dissolved in a suitable solvent and then crystallized and agglomerated using an antisolvent in the presence of an agglomeration liquid.

The object of the present invention is achieved by the process according to the invention for the production of the inventive active compound product of the compound of formula (I), the inventive active compound product of the compound of formula (I) and the improved properties thereof for example in respect of the isolability of the active compound product, the dischargeability of the active compound product after isolation and drying and also conveyability, sieveability and micronizability. The object is further achieved when a defined modification of the active compound product of the compound of formula (I) is formed. It is preferable when the crystalline form of modification I is formed. The object is further achieved when the process according to the invention does not result in the formation of hydrates or dihydrates of the active compound product of the compound of formula (I).

According to the present invention the inventive active compound product of the compound of formula (I) having improved properties for example in respect of the isolability of the active compound product, the dischargeability of the active compound product after isolation and drying and also conveyability, sieveability and micronizability is produced in a process comprising the following steps:
a) The compound of formula (I) in solid form is dissolved at elevated temperature in a suitable (polar and/or aprotic) solvent or in a suitable (polar and/or aprotic) solvent in combination with at least one wetting agent.
  i. This may optionally be followed by a clarifying filtration.
b) The compound of formula (I) dissolved according to step a) is crystallized out of the solution by addition of an antisolvent or an antisolvent in combination with at least one wetting agent
  or
  an antisolvent or an antisolvent in combination with at least one wetting agent is initially charged and the compound of formula (I) dissolved according to step a) is added.
c) The suspension formed is cooled to a lower temperature.
d) An agglomerization liquid is added to form the active compound product.
e) The active compound product formed in step d) is isolated, washed and dried.
f) The active compound product isolated and dried in step e) is optionally comminuted.

Scheme 1 depicts by way of example the individual reaction steps for producing the inventive active compound product of the compound of formula (I) having improved properties.

Scheme 1

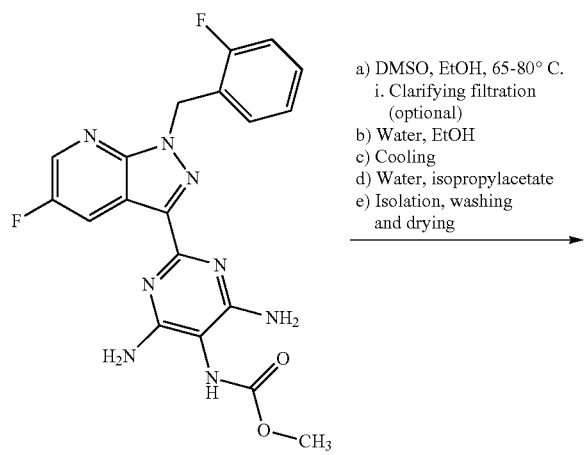

Compound of formula (I)
as arbitrary solvate (e.g.
Di-DMSO solvate) or ansolvate a) DMSO, EtOH, 65-80° C.
  i. Clarifying filtration (optional)
b) Water, EtOH
c) Cooling
d) Water, isopropylacetate
e) Isolation, washing and drying

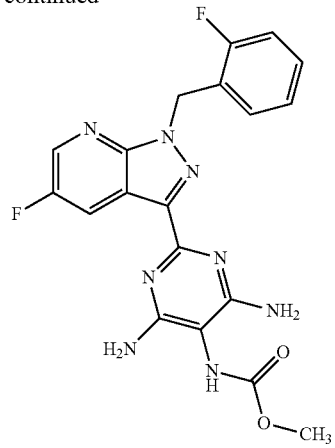

Active compound product
of the compound of formula (I)
with inventive properties In the context of the present invention improved isolability of the active compound product, dischargeability of the active compound product after isolation and drying and also conveyability, sieveability and micronizability of the active compound product of the compound of formula (I) are to be understood as meaning the following, for example:

Improved isolability is measurable on an industrial scale for example via a higher area-specific throughput in an inverting filter centrifuge (example 15).

Improved dischargeability from the isolation apparatus is measurable for example via the maximum filtercake thickness at which the discharge path, for example out of the inverting filter centrifuge, does not become blocked.

Improved drying is measurable for example via unproblematic drying in a vacuum contact dryer for example and avoidance of blockages in the drop shaft upon discharging from the dryer.

Improved sieveability is measurable for example via improved feeding into the industrial sieving machine as a result of improved flowability of the active compound product and via fewer sieve blockages, for example via the throughput of active compound product per unit time (example 16).

Improved micronization is measurable for example via easier feeding of the active compound product into the jet mill.

In the context of the present invention, "industrial scale" is defined as a batch size of >10 kg of active compound.

In the context of the present invention the isolation of the active compound product is carried out using for example a filter centrifuge, for example an inverting filter centrifuge.

In the context of the present invention the drying of the active compound product is carried out using for example a vacuum contact dryer, for example a spherical dryer.

In the context of the present invention the sieving of the active compound product is carried out for example using a Frewitt Coniwitt TC200 sieving machine (sieve aperture diameter 3 mm) or a Frewitt Oscillowitt MG-800 sieving machine (sieve aperture diameter 2.5 to 4.0 mm).

In the context of the present invention micronization is carried out for example by comminution in a jet mill.

WO 2013/076168 is considered to be the closest prior art. WO 2013/076168 describes a process for producing the compound of formula (I) (route 1) which as described hereinabove results in an active compound product that causes problems during workup. These problems during workup impede production of the pharmaceutical active compound of formula (I) on an industrial scale.

Surprisingly, compared to the active compound product of the compound of formula (I) produced by the process according to WO 2013/076168 (route 1) the active compound product of the compound of formula (I) produced by the process according to the invention (route 2) showed improved properties inter alia in respect of the isolability of the active compound product, the dischargeability of the active compound product after isolation and drying and also conveyability, sieveability and micronizability.

Figure 2:

The object of the present invention, i.e. improved isolability of the active compound product, dischargeability of the active compound product after isolation and drying and also conveyability, sieveability and micronizability of the inventive active compound product of the compound of formula (I), is solved as follows:

FIG. 1 shows a scanning electron microscopy image of the active compound product (I) produced by the process according to WO 2013/076168 (route 1). FIG. 2 shows a scanning electron microscopy image of the active compound product (I) produced by the process according to the invention (route 2). These images show a marked difference in the structure of the active compound product which points to the improved properties inter alia in respect of the isolability of the active compound product, the dischargeability of the active compound product after isolation and drying and also conveyability, sieveability and micronizability of the active compound product produced by the process according to the invention.

The isolability of the material produced via route 2 is improved compared to the material produced via route 1. This manifests for example in a higher area-specific throughput in the inverting filter centrifuge. On an industrial scale isolation of the material from route 1 achieved an average area-specific throughput of 1.6 kg/m²h. The average area-specific throughput of the material from route 2 was 3.0 kg/m²h and thus nearly double the above (example 15).

Improved dischargeability from the isolation apparatus: The process according to route 2 prevents the formation of a felt-like filtercake having high tear strength. Both after isolation in the pressure filter and after isolation in the filter centrifugation the filtercake is soft and moldable. This prevents blockage of the discharge path. For example on an industrial scale a blockage of the discharge path from the inverting filter centrifuge after isolation of the material from Route 1 was avoidable only by reducing the filtercake thickness to 8 to 9 mm. By contrast in the isolation of the material from route 2 an average filtercake height of 25 mm was realized without any blocking of the discharge path being observed.

Improved drying: Due to the soft consistency and good deformability of the filtercake from the process of route 2 drying in the vacuum contact dryer (e.g. spherical dryer) is unproblematic. The dried material forms a readily flowable bulk material which does not result in blockages of the drop shaft upon discharging from the dryer either.

Improved sieveability: The material from the process of route 2 is easy to feed into the sieving machine on account of its good flowability. Sieving results in markedly fewer sieve blockages than for material from the process according to route 1. For example on an industrial scale 65 kg of the material from route 2 were sievable in <5 min in a Frewitt Coniwitt TC200 sieving machine (sieve aperture diameter 3 mm). This corresponds to >13 kg/min. For comparison sieving material from route 1 via a Frewitt Oscillowitt MG-800 sieving machine (sieve aperture diameter 2.5 to 4.0 mm) only achieved throughputs of <10 kg/h. This corresponds to <0.17 kg/min (example 16). Observed here is a very large difference of a factor of nearly 100 in the sieve throughput of the active compound product of route 1 compared to the active compound product of route 2. This very large difference in sieve throughput results predominantly from the material characteristics of the active compound product and cannot be explained by the different machine types.

The solids handling and solids conveying properties are markedly improved.

Improved micronization: The material from the process of route 2 is easy to feed into the jet mill on account of its good flowability.

As shown in example 10 and table 2, a further advantage of the process according to the invention is apparent during production of the granulating liquid for tableting. Incorporation of the active compound product produced by the process according to the invention does require slightly more water, thus insignificantly prolonging spray times during granulation. On the other hand the incorporation time required to introduce the active compound into the granulating suspension before homogenization thereof is significantly shortened. Altogether, this results in a process which is expedited and more manageable compared to the process described in WO 2013/076168 beschriebenen Verfahren (route 1).

A further advantage of the process according to the invention is that compared to the process described in WO 2013/076168 (route 1) it provides a broader applicability for different granulation processes. As described in example 11 the process described in WO 2013/076168 (route 1) may employ the process of fluidized bed granulation and the process of wet dispersion while the process of rapid mixer granulation is employable only to a limited extent and the process of dry compaction is not employable. By contrast, all of the abovementioned granulation processes are employable for the active compound product produced by the process according to the invention (route 2).

A further advantage of the process according to the invention is that—compared to the active compound product produced by the process described in WO 2013/076168 (route 1)—the active compound product produced by the process according to the invention allows for easier discrimination of off-specification particle sizes from on-specification particle sizes by means of release kinetics (release method according to example 14). This is shown for the batches of table 8 in FIGS. 6 and 7.

Based on the prior art it could not have been expected that the process according to the invention results in an active compound product which compared to the product from the prior art process shows such markedly improved properties in industrial scale production of the pharmaceutical active compound of formula (I) in a solid dosage form. Nor could it have been expected based on the prior art that the process according to the invention results in a defined modification of the active compound of formula (I), preferably in the crystalline form of modification I. It was likewise surprising that no hydrates or dihydrates of the active compound of formula (I) were formed during production of the active compound product according to the invention. Under certain conditions the active compound forms hydrates upon contact with water. This is surprisingly prevented in the process according to the invention.

There is also no indication in the prior art that adhering to the sequence of the washing steps (initially with ethanol, then with isopropyl acetate) during the washing in the course of isolation and drying according to step e) is crucial. Nor is it discernible from the prior art that drying with a nitrogen stream makes it possible to afford a DMSO-free product.

U.S. Pat. No. 5,994,538 and US2016083416 describe agglomeration processes. These differ from the process according to the invention in a multiplicity of points. None of the documents describes the use of a wetting agent. In contrast to the present invention, in US2016083416 the agglomerates produced are milled to produce microparticles that cannot be produced in the conventional way. Improvements in terms of filterability, flowability and formulability of the agglomerates are not described. A further difference compared to US2016083416 is for example that according to US2016083416 the drying of the agglomerates results in at least partial deagglomeration. This was not observed for the agglomerates according to the invention. US2016083416 employs exclusively ethers as the agglomeration liquid while the process according to the invention preferably employs acetates. In contrast to the present invention U.S. Pat. No. 5,994,538 relates to an intermediate and not to a pharmaceutical active compound. Aspects important to the present invention such as production of a defined polymorphic form, removal of solvent residues after drying or else formulation are not described in U.S. Pat. No. 5,994,538. The process described in U.S. Pat. No. 5,994,538 for producing spherical agglomerates of 10-phenothiazinylpropanoic acid is characterized in that a suspension of 10-phenothiazinylpropanoic acid in water is stirred directly in the presence of a water-immiscible agglomerization liquid. The inventive steps a), b) and c) are not performed.

One embodiment of the present invention comprises a process for producing an active compound product of the compound of formula (I)

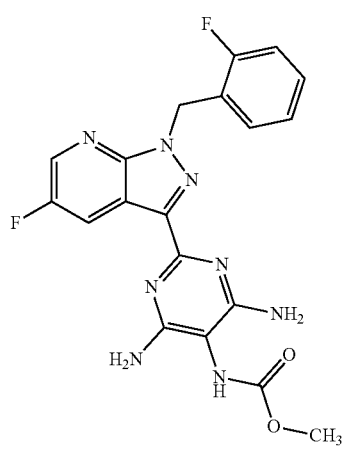

(I)

wherein
a) the compound of formula (I) in solid form is dissolved at a temperature of 30-100° C. in one or more polar and/or aprotic solvents or in one or more polar and/or aprotic solvents in combination with at least one wetting agent selected from the group consisting of methanol, ethanol, n-propanol, isopropanol, tetrahydrofuran, acetonitrile, acetone, methyl ethyl ketone, 1,4-dioxane and methyl-THF, b) the dissolved compound of formula (I) is subsequently crystallized out of the solution by addition of water as antisolvent or of water in combination with at least one wetting agent selected from the group consisting of methanol, ethanol, n-propanol, isopropanol, tetrahydrofuran, acetonitrile, acetone, methyl ethyl ketone, 1,4-dioxane and methyl-THF, wherein the ratio of water to the at least one wetting agent added in step a) or b) is 1:0-20:1 w/w and the addition of water or of the combination of water with at least one wetting agent is carried out at a temperature of 30-100° C. and over a duration of 0.1 min-1200 min, or water as antisolvent or water in combination with at least one wetting agent is initially charged and the compound of formula (I) dissolved according to step a) is added, wherein the at least one wetting agent, the ratio of water to the at least one wetting agent added in step a) and/or b), the temperature and the duration over which the addition of the dissolved compound is carried out are as specified above;

c) the suspension formed is subsequently cooled to a temperature of 5-50° C. at a cooling rate of 1-60 K/h and d) the active compound crystallized out in step b) is subsequently agglomerated to afford active compound product by addition of an agglomeration liquid, wherein in the case where a wetting agent was added in step a) and/or b) the ratio of the mass of the agglomeration liquid to the sum of the mass of the compound of formula (I) plus the mass of the at least one wetting agent added in step a) and/or b) is 0.3 to 2.0.

A further embodiment of the present invention comprises a process for producing an active compound product of the compound of formula (I)

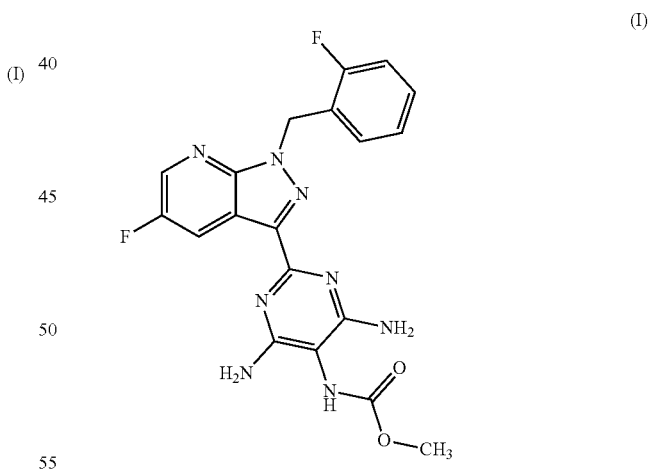

(I)

in the crystalline form of modification I, wherein
a) the compound of formula (I) in solid form is dissolved at a temperature of 30-100° C. in one or more polar and/or aprotic solvents or in one or more polar and/or aprotic solvents in combination with at least one wetting agent selected from the group consisting of methanol, ethanol, n-propanol, isopropanol, tetrahydrofuran, acetonitrile, acetone, methyl ethyl ketone, 1,4-dioxane and methyl-THF, b) the dissolved compound of formula (I) is subsequently crystallized out of the solution by addition of water as antisolvent or of water in combination with at least one wetting agent selected from the group consisting of methanol, ethanol, n-propanol, isopropanol, tetrahydrofuran, acetonitrile, acetone, methyl ethyl ketone, 1,4-dioxane and methyl-THF, wherein the ratio of water to the at least one wetting agent added in step a) or b) is 1:0-20:1 w/w and the addition of water or of the combination of water with at least one wetting agent is carried out at a temperature of 30-100° C. and over a duration of 0.1 min-1200 min, or water as antisolvent or water in combination with at least one wetting agent is initially charged and the compound of formula (I) dissolved according to step a) is added, wherein the at least one wetting agent, the ratio of water to the at least one wetting agent added in step a) and/or b), the temperature and the duration over which the addition of the dissolved compound is carried out are as specified above;

c) the suspension formed is subsequently cooled to a temperature of 5-50° C. at a cooling rate of 1-60 K/h and d) the active compound crystallized out in step b) is subsequently agglomerated to afford active compound product by addition of an agglomeration liquid, wherein in the case where a wetting agent was added in step a) and/or b) the ratio of the mass of the agglomeration liquid to the sum of the mass of the compound of formula (I) plus the mass of the at least one wetting agent added in step a) and/or b) is 0.3 to 2.0.

A further embodiment of the present invention comprises a process for producing active compound product of the compound of formula (I), wherein a) the compound of formula (I) in solid form is dissolved at a temperature of 50-90° C. in one or more polar and/or aprotic solvents or in one or more polar and/or aprotic solvents in combination with at least one wetting agent selected from the group consisting of methanol, ethanol, n-propanol and isopropanol, b) the dissolved compound of formula (I) is subsequently crystallized out of the solution by addition of water as antisolvent or of water in combination with at least one wetting agent selected from the group consisting of methanol, ethanol, n-propanol and isopropanol, wherein the ratio of water to the wetting agent added in step a) or b) is 1:0 to 12:1 w/w and the addition of water or of the combination of water with at least one wetting agent is carried out at a temperature of 50-90° C. and over a period of 0.1 min-360 min, or water as antisolvent or water in combination with at least one wetting agent is initially charged and the compound of formula (I) dissolved according to step a) is added, wherein the at least one wetting agent, the ratio of water to the at least one wetting agent, the temperature and the duration over which the addition of the dissolved compound is carried out are as specified above;

c) the suspension formed is subsequently cooled to a temperature of 10-30° C. at a cooling rate of 5-45 K/h and d) the active compound crystallized out in step b) is subsequently agglomerated to afford active compound product by addition of an agglomeration liquid, wherein in the case where a wetting agent was added in step a) and/or b) the ratio of the mass of agglomeration liquid to the sum of the mass of compound of formula (I) plus the mass of the wetting agent added in step a) or b) is 0.5 to 1.5 w/w.

A further embodiment of the present invention comprises a process for producing active compound product of the compound of formula (I) in the crystalline form of modification I, wherein a) the compound of formula (I) in solid form is dissolved at a temperature of 50-90° C. in one or more polar and/or aprotic solvents or in one or more polar and/or aprotic solvents in combination with at least one wetting agent selected from the group consisting of methanol, ethanol, n-propanol and isopropanol, b) the dissolved compound of formula (I) is subsequently crystallized out of the solution by addition of water as antisolvent or of water in combination with at least one wetting agent selected from the group consisting of methanol, ethanol, n-propanol and isopropanol, wherein the ratio of water to the wetting agent added in step a) or b) is 1:0 to 12:1 w/w and the addition of water or of the combination of water with at least one wetting agent is carried out at a temperature of 50-90° C. and over a period of 0.1 min-360 min, or water as antisolvent or water in combination with at least one wetting agent is initially charged and the compound of formula (I) dissolved according to step a) is added, wherein the at least one wetting agent, the ratio of water to the at least one wetting agent, the temperature and the duration over which the addition of the dissolved compound is carried out are as specified above;

c) the suspension formed is subsequently cooled to a temperature of 10-30° C. at a cooling rate of 5-45 K/h and d) the active compound crystallized out in step b) is subsequently agglomerated to afford active compound product by addition of an agglomeration liquid, wherein in the case where a wetting agent was added in step a) and/or b) the ratio of the mass of agglomeration liquid to the sum of the mass of compound of formula (I) plus the mass of the wetting agent added in step a) or b) is 0.5 to 1.5 w/w.

A further embodiment of the present invention comprises a process for producing active compound product of the compound of formula (I), wherein a) the compound of formula (I) in solid form is dissolved at a temperature of 65-80° C. in DMSO as solvent with ethanol as wetting agent, b) the dissolved compound of formula (I) is subsequently crystallized out of the solution by addition of water as antisolvent, wherein the ratio of water to the ethanol added in step a) is 1:0 w/w to 3:1 w/w and the addition of the antisolvent is carried out at a temperature of 65-80° C. and over a period of 0.1-60 min, or water as antisolvent is initially charged and the compound of formula (I) dissolved in DMSO and ethanol according to step a) is added, wherein ethanol, the ratio of water to ethanol, the temperature and the duration over which the addition of the dissolved compound is carried out are as specified above;

c) the suspension formed is subsequently cooled to a temperature of 15-25° C. at a cooling rate of 5-35 K/h and d) the active compound crystallized out in step b) is subsequently agglomerated to afford active compound product by addition of an agglomeration liquid, wherein in the case where a wetting agent was added in step a) and/or b) the ratio of the mass of agglomeration liquid to the sum of the mass of the compound of formula (I) plus the mass of the wetting agent added in step a) or b) is 0.85 to 1.3 w/w.

A further embodiment of the present invention comprises a process for producing active compound product of the compound of formula (I) in the crystalline form of modification I, wherein
- a) the compound of formula (I) in solid form is dissolved at a temperature of 65-80° C. in DMSO as solvent with ethanol as wetting agent,
- b) the dissolved compound of formula (I) is subsequently crystallized out of the solution by addition of water as antisolvent, wherein the ratio of water to the ethanol added in step a) is 1:0 w/w to 3:1 w/w and the addition of the antisolvent is carried out at a temperature of 65-80° C. and over a period of 0.1-60 min, or water as antisolvent is initially charged and the compound of formula (I) dissolved in DMSO and ethanol according to step a) is added, wherein ethanol, the ratio of water to ethanol, the temperature and the duration over which the addition of the dissolved compound is carried out are as specified above;
- c) the suspension formed is subsequently cooled to a temperature of 15-25° C. at a cooling rate of 5-35 K/h and
- d) the active compound crystallized out in step b) is subsequently agglomerated to afford active compound product by addition of an agglomeration liquid, wherein in the case where a wetting agent was added in step a) and/or b) the ratio of the mass of agglomeration liquid to the sum of the mass of the compound of formula (I) plus the mass of the wetting agent added in step a) or b) is 0.85 to 1.3 w/w.

a) Dissolution in a Suitable Solvent

The compound of formula (I) in solid form is dissolved in one or more polar and/or aprotic solvents or in one or more polar and/or aprotic solvents in combination with at least one wetting agent.

Examples of the compound of formula (I) in solid form are any desired solvents or ansolvates, for example modifications I to V described in WO 2013/076168, the amorphous form, a dimethylformamide-water solvate, a didimethylsulfoxide solvate, a triacetic acid solvate, a monohydrate and a dihydrate. In one embodiment of the present invention the employed compound of formula (I) in solid form is a didimethyl sulfoxide solvate.

In one embodiment of the present invention the at least one polar and/or aprotic solvent in step a) is selected from the group consisting of DMSO, N-methyl-2-pyrrolidone (NMP), dimethylacetamide (DMAc) and dimethylformamide (DMF) or combinations thereof with at least one wetting agent selected from the group consisting of methanol, ethanol, n-propanol, isopropanol, tetrahydrofuran, acetonitrile, acetone, methyl ethyl ketone, 1,4-dioxane and methyl-THF.

In a further embodiment of the present invention step a) employs DMSO as solvent and no wetting agent is added.

In a further embodiment of the present invention step a) employs DMSO as solvent in combination with ethanol as wetting agent, wherein the ratio between DMSO and ethanol is 1:0 to 5:1 w/w. In a further embodiment of the present invention step a) employs DMSO as solvent in combination with ethanol as wetting agent, wherein the ratio between DMSO and ethanol is 1:0 to 4:1 w/w. In a further embodiment of the present invention step a) employs DMSO as solvent in combination with ethanol as wetting agent, wherein the ratio between DMSO and ethanol is 1:0 to 3.9:1 w/w.

The dissolving is carried out at a temperature of 30-100° C. In a further embodiment of the present invention the dissolving is carried out at a temperature of 50-90° C. In a further embodiment of the present invention the dissolving is carried out at a temperature of 65-80° C.

The compound of formula (I) is present in the solvent or the combination of solvent and at least one wetting agent in a concentration of 3-50%. In a further embodiment of the present invention the compound of formula (I) is present in the solvent or the combination of solvent and at least one wetting agent in a concentration of 3-30%. In a further embodiment of the present invention the compound of formula (I) is present in the solvent or the combination of solvent and at least one wetting agent in a concentration of 3-15%.

a) i. Filtration

The solution obtained according to step a) is optionally subjected to a clarifying filtration.

b) Crystallization with Antisolvent

A further embodiment of the present invention is the process according to the invention, wherein in step b) the dissolved compound of formula (I) is subsequently crystallized out of the solution by addition of water as antisolvent or of water in combination with at least one wetting agent selected from the group consisting of methanol, ethanol, n-propanol and isopropanol, wherein the ratio of water to the at least one wetting agent added in step a) or b) is 1:0-20:1 w/w and the addition of water or of the combination of water with at least one wetting agent is carried out at a temperature of 30-100° C. and over a period of 0.1 min-1200 min, or water as antisolvent or water in combination with at least one wetting agent is initially charged and the compound of formula (I) dissolved according to step a) is added, wherein the at least one wetting agent, the ratio of water to the at least one wetting agent added in step a) and/or b), the temperature and the duration over which the addition of the dissolved compound is carried out are as specified above.

In a further embodiment of the present invention the ratio of water to the at least one wetting agent added in step a) or b) is 1:0-12:1 w/w. In a further embodiment of the present invention the ratio of water to the at least one wetting agent added in step a) or b) is 1:0-3:1 w/w.

In a further embodiment of the present invention step b) comprises carrying out the addition of the antisolvent or of the antisolvent in combination with at least one wetting agent at a temperature of 50-90° C. In a further embodiment of the present invention the addition of the antisolvent or of the antisolvent in combination with at least one wetting agent is carried out at a temperature of 65-80° C.

In a further embodiment of the present invention step b) comprises carrying out the addition of the antisolvent or of the antisolvent in combination with at least one wetting agent over a duration of 0.1 min-360 min. In a further embodiment of the present invention the addition of the antisolvent or of the antisolvent in combination with at least one wetting agent is carried out over a duration of 0.1 min-60 min.

In one embodiment of the present invention step b) employs water as antisolvent in combination with ethanol as wetting agent.

In one embodiment of the process according to the invention at least one wetting agent is added in step a) and no wetting agent is added in step b).

In a further embodiment of the process according to the invention no wetting agent is added in step a) and at least one wetting agent is added in step b).

In a further embodiment of the process according to the invention at least one wetting agent is added in step a) and in step b).

In a further embodiment of the process according to the invention no wetting agent is added in step a) nor in step b).

The process may be carried out with or without seeding by addition of the compound of formula (I) in the crystalline form of modification I. The production of the seed crystals of the compound of formula (I) is carried out, by way of example, analogously to WO 2013/076168, example 13, methods E and F.

c) Cooling

In one embodiment of the present invention the suspension formed is cooled to a temperature of 5-50° C. at a cooling rate of 1-60 K/h or 5-45 K/h or 5-35 K/h. In a further embodiment of the present invention the suspension formed is cooled to a temperature of 10-30° C. at a cooling rate of 1-60 K/h or 5-45 K/h or 5-35 K/h. In a further embodiment of the present invention the suspension formed is cooled to a temperature of 15-25° C. at a cooling rate of 1-60 K/h or 5-45 K/h or 5-35 K/h.

In one embodiment of the present invention the suspension formed is cooled to a temperature of 5-50° C. or 10-30° C. or 15-25° C. at a cooling rate of 1-60 K/h. In a further embodiment of the present invention the suspension formed is cooled to a temperature of 5-50° C. or 10-30° C. or 15-25° C. at a cooling rate of 5-45 K/h. In a further embodiment of the present invention the suspension formed is cooled to a temperature of 5-50° C. or 10-30° C. or 15-25° C. at a cooling rate of 5-35 K/h.

d) Agglomeration with Agglomeration Liquid

Employed as the agglomeration liquid are esters only sparingly miscible with water, for example methyl acetate, ethyl acetate, n-propyl acetate, isopropyl acetate, n-butyl acetate, isobutyl acetate, methyl propanoate, ethyl propanoate, n-propyl propanoate, isopropyl propanoate, n-butyl propanoate, isobutyl propanoate, methyl butanoate, ethyl butanoate, n-propyl butanoate, isopropyl butanoate, n-butyl butanoate or isobutyl butanoate; ethers only sparingly miscible with water, for example dimethyl ether, diethyl ether, ethyl methyl ether, di-n-propyl ether, ethyl n-propyl ether, methyl tert-butyl ether or tetrahydrofuran; ketones only sparingly miscible with water, for example methyl ethyl ketone or 2-pentanone; or organochlorides only sparingly miscible with water, for example $CCl_4$, $CHCl_3$, $CH_2Cl_2$, $CH_3Cl$, or $C_2H_4Cl_2$; or toluene.

In one embodiment of the present invention the agglomeration liquid is selected from the group consisting of esters selected from methyl acetate, ethyl acetate, n-propyl acetate, isopropyl acetate, n-butyl acetate, isobutyl acetate, methyl propanoate, ethyl propanoate, n-propyl propanoate, isopropyl propanoate, n-butyl propanoate, isobutyl propanoate, methyl butanoate, ethyl butanoate, n-propyl butanoate, isopropyl butanoate, n-butyl butanoate and isobutyl butanoate; ethers selected from dimethyl ether, diethyl ether, ethyl methyl ether, di-n-propyl ether, ethyl n-propyl ether, methyl tert-butyl ether and tetrahydrofuran; ketones selected from methyl ethyl ketone and 2-pentanone; organochlorides selected from $CCl_4$, $CHCl_3$, $CH_2Cl_2$, $CH_3Cl$, or $C_2H_4Cl_2$; and toluene. In a further embodiment of the present invention the employed agglomeration liquid is an ester; in a further embodiment of the present invention the employed agglomeration liquid is an acetate; in a further embodiment of the present invention the employed agglomeration liquid is isopropyl acetate.

A prerequisite for the formation of agglomerates is that the solvent system consists of two liquid phases. The ratio of the mass of the agglomeration liquid to the sum of the mass of the compound of formula (I) plus the mass of the at least one wetting agent added in step a) or b) is 0.3 to 2.0 w/w. The ratio may be calculated by the following formula:

Agglomeration liquid w/w/(compound of formula (I) w/w+wetting agent w/w)=0.3-2.0 w/w In a further embodiment the ratio of the mass of the agglomeration liquid to the sum of the mass of the compound of formula (I) plus the mass of the at least one wetting agent added in step a) or b) is 0.5 to 1.5 w/w. In a further embodiment the ratio of the mass of the agglomeration liquid to the sum of the mass of the compound of formula (I) plus the mass of the at least one wetting agent added in step a) or b) is 0.85 to 1.3 w/w.

The addition of the agglomeration liquid is carried out over a duration of 0.1 to 1200 min or 0.1 to 360 min or 0.1 to 60 min at a temperature of 5-50° C. or 10-30° C. or 15-25° C.

This is followed by aging by stirring over a duration of 0.1 min to 5 days, 0.1 min-1200 min or 0.1 min-360 min or 0.1 min-60 min.

e) Isolating, Washing and Drying

The active compound product is isolated and washed. In one embodiment the active compound product is washed initially with a $C_1$-$C_4$ alcohol and subsequently with an acetate selected from methyl acetate, ethyl acetate, n-propyl acetate, isopropyl acetate, n-butyl acetate and isobutyl acetate. In a further embodiment the active compound product is washed initially with ethanol and subsequently with isopropyl acetate.

In one embodiment of the present invention the drying is carried out under reduced pressure with a nitrogen stream at a temperature of 15-75° C. In a further embodiment of the present invention the drying is carried out at a temperature of 25-70° C. In a further embodiment of the present invention the drying is carried out at a temperature of 25-65° C.

The yield is between 72% and 96% of theory. A DMSO-free product is obtained.

f) Optional Comminution

After isolation and drying the active compound product according to the invention is sieved and optionally comminuted by micronization (for example comminution using a jet mill) or using wet milling.

One embodiment of the present invention comprises an active compound product of the compound of formula (I) produced by the process according to the invention, wherein the active compound product has one or more of the following properties: improved isolability of the active compound product, improved dischargeability of the active compound product after isolation and drying and also improved conveyability, sieveability and micronizability, wherein the improved properties are as defined above.

A further embodiment of the present invention comprises an active compound product produced by the process according to the invention, wherein the active compound product exhibits at least the properties of improved isolability measured as an elevated average area-specific throughput for isolation using a centrifuge and an improved sieveability measured at an elevated sieve throughput.

A further embodiment of the present invention comprises an active compound product produced by the process according to the invention, wherein after the isolating, washing and drying in step e) the active compound product contains no DMSO.

A further embodiment of the present invention comprises solid dosage forms containing the active compound product produced by route 2.

The production of the solid dosage forms may be carried out in the form of direct mixing/dry compaction or via a wet granulation process (rapid mixer granulation or fluidized bed granulation). The tabletting is preferably carried out with the initially produced granulate. This may be followed by a coating of the solid dosage forms.

In wet granulation the active compound product may be initially charged in the premix (initial charge) as a solid or it is suspended in the granulating liquid. The employed granulating liquid contains a solvent and a hydrophilic binder. The hydrophilic binder is dispersed in the granulating fluid or preferably dissolved therein. Employable solvents for the granulating liquid include organic solvents, for example ethanol or acetone or water or mixtures thereof. It is preferable when water is used as solvent. Hydrophilic binders employed are pharmaceutically acceptable hydrophilic additives, preferably those which dissolve in the solvent of the granulating fluid. Preferably employed here are hydrophilic polymers such as for example hydroxypropylmethylcellulose (HPMC), sodium carboxymethylcellulose, methylcellulose, hydroxypropylcellulose (HPC), low-substituted hydroxypropylcellulose (L-HPC), hydroxypropylcellulose LF, polyvinylpyrrolidone, polyvinyl alcohol, vinylpyrrolidone-vinyl acetate copolymers (for example Kollidon® VA64, BASF), gelatin, guar gum, partially hydrolyzed starch, alginates or xanthan. It is particularly preferable to use hydroxypropylmethylcellulose (HPMC) as a hydrophilic binder. The hydrophilic binder is present at a concentration of 1% to 12% (based on the total mass of the pharmaceutical dosage form), preferably 1% to 6%.

The premix (initial charge) of the wet granulation contains further pharmaceutically acceptable additives, such as for example fillers, dry binders and disintegration promoters (disintegrants). Fillers and dry binders are for example cellulose powder, microcrystalline cellulose, silicified microcrystalline cellulose, lactose monohydrate, mannitol, maltitol, sorbitol and xylitol, preferably microcrystalline cellulose or mannitol or a mixture of microcrystalline cellulose and mannitol/lactose monohydrate. Disintegration promoters (disintegrants) are for example carboxymethylcellulose, croscarmellose (crosslinked carboxymethylcellulose), crospovidone (crosslinked polyvinylpyrrolidone), low-substituted hydroxypropylcellulose (L-HPC), sodium carboxymethyl starch, potato sodium starch glycolate, partially hydrolyzed starch, wheat starch, maize starch, rice starch and potato starch.

The obtained granulate is subsequently converted into solid dosage forms. Pharmaceutically acceptable additives added are, for example, lubricants, glidants, flow regulators and disintegration promoters (disintegrants). Lubricants, glidants, flow regulators are for example fumaric acid, stearic acid, sodium stearyl fumarate, magnesium stearate, higher molecular weight fatty alcohols, starches (wheat, rice, maize or potato starch), talc, high-dispersity (colloidal) silicon dioxide and glycerol distearate. Disintegration promoters (disintegrants) are for example carboxymethylcellulose, croscarmellose (crosslinked carboxymethylcellulose), crospovidone (crosslinked polyvinylpyrrolidone), low-substituted hydroxypropylcellulose (L-HPC), sodium carboxymethyl starch, partially hydrolyzed starch, wheat starch, maize starch, rice starch and potato starch.

Solid dosage forms are optionally coated under customary conditions familiar to those skilled in the art in a further step. The coating is effected by addition of coating and film-forming agents such as hydroxypropylcellulose, hydroxypropylmethylcellulose (for example hydroxypropylmethylcellulose 5 cP or 15 cP), polyvinylpyrrolidone, vinylpyrrolidone-vinyl acetate copolymers (for example Kollidon® VA64, BASF), shellac, glyceryl triacetate, triethyl citrate, talc as an antiadhesive agent and/or colourants/pigments such as titanium dioxide, iron oxides, indigotin or suitable coloured coatings.

One embodiment of the present invention comprises solid dosage forms containing active compound product of the compound of formula (I) produced by a process according to the invention and further containing microcrystalline cellulose, lactose monohydrate, hydroxypropylmethylcellulose 3 cP and/or 5 cP, sodium lauryl sulfate or polysorbate 20, sodium croscarmellose, magnesium stearate, talc, iron oxides and titanium dioxide.

A further embodiment of the present invention comprises solid dosage forms containing active compound product of the compound of formula (I) produced by a process according to the invention, wherein the solid dosage forms contain 1.25 to 20 mg of the active compound product of the compound of formula (I) per solid dosage form. Further embodiments comprise solid dosage forms containing 1.25 mg, 2.5 mg, 5.0 mg, 7.5 mg, 10 mg, 12.5 mg, 15 mg, 17.5 mg or 20 mg of active compound product of the compound of formula (I) produced by a process according to the invention per solid dosage form.

The present invention is illustrated in more detail hereinbelow with reference to non-limiting preferred examples and comparative examples. Unless otherwise stated all recited amounts refer to weight percentages.

The objective of examples 1 to 3, 5 and 6 was the development of the process according to the invention for producing the active compound product according to the invention. Example 4 describes an inventive process achieving the specification of the active compound of formula (I). Example 4 also comprises the washing steps and the drying process which are relevant to achieving the specification and result in a DMSO-free product. The washing steps comprised in example 4 and the drying process are performed analogously for examples 5 and 6 according to the process of the present invention.

A. EXAMPLES

Abbreviations

| | |
|---|---|
| DMAc | Dimethylacetamide |
| DMF | Dimethylformamide |
| DMSO | Dimethyl sulfoxide |
| o. t. | Of theory (in chemical yield) |
| Et | Ethyl |
| EtOH | Ethanol |
| h | Hour(s) |
| HPMC 5cP | Hydroxypropylmethylcellulose 5 cP. A 2% aqueous solution of HPMC 5cP has a viscosity of 5 mPas at 20° C. |
| HPMC 3cP | Hydroxypropylmethylcellulose 3 cP. A 2% aqueous solution of HPMC 3cP has a viscosity of 2.4-3.6 mPas at 20° C. |

-continued

| | |
|---|---|
| HPC SSL | Hydroxypropylcellulose SSL. A 2% aqueous solution of HPC SSL has a viscosity of 2-2.9 mPas at 20° C. |
| Me | Methyl |
| micron. | Micronized |
| min | Minute(s) |
| MS | Mass spectrometry |
| AV | average value |
| N | newtons |
| NMP | N-methyl-2-pyrrolidone |
| NMR | Nuclear magnetic resonance spectrometry |
| o. | Oval |
| r. | Round |
| Route 1 | Process according to WO 2013/076168 |
| Route 2 | Process according to the invention |
| r.H. | Relative humidity |
| RT | Room temperature |
| THF | Tetrahydrofuran |
| CR | Curvature radius |
| w/w | weight to weight ratio |
| $X_{10\%}$, $X_{50\%}$, $X_{90\%}$ | Diameter below which 10%, 50% and 90% respectively of the particles in an analyzed sample lie |

Example 1

8.85 g of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I, produced as per example 13, method E of WO 2013/076168 were heated to 75° C. in 35.8 g of DMSO. Added to the resulting clear solution over 360 min were 125.7 g of a water-ethanol mixture (4:1 w/w, RT). Once the first 0.5 g of the ethanol-water mixture had been added the solution was seeded with 59 mg of crystalline methyl {4,6-diamino-2-[5-fluoro-1-(2-fluorobenzyl)-1H-pyrazolo [3,4-b]pyridin-3-yl]pyrimidin-5-yl}carbamate in the crystalline form of modification I, produced as per example 13, method E of WO 2013/076168. After addition of the remaining amount of ethanol-water mixture the suspension formed was slowly cooled to 20° C. (at a rate of 10 K/h). Added to this suspension over 60 minutes at 20° C. were 34.0 g of isopropyl acetate. The mixture was stirred at 20° C. for a further 60 min before the solid was separated off, washed and dried under reduced pressure. This afforded methyl {4,6-diamino-2-[5-fluoro-1-(2-fluorobenzyl)-1H-pyrazolo [3,4-b]pyridin-3-yl]pyrimidin-5-yl}carbamate of formula (I) in the crystalline form of modification I in the form of the inventive active compound product.

Yield: 7.66 g (86.6% o. t.)

Example 2

8.85 g of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I, produced as per example 13, method E of WO 2013/076168 were heated to 75° C. in 35.9 g of DMSO. Added to the resulting clear solution over 360 min were 125.7 g of a water-ethanol mixture (9:1 w/w, RT). Once the first 0.5 g of the water-methanol mixture had been added the solution was seeded with 59 mg of crystalline methyl {4,6-diamino-2-[5-fluoro-1-(2-fluorobenzyl)-1H-pyrazolo [3,4-b]pyridin-3-yl]pyrimidin-5-yl}carbamate in the crystalline form of modification I, produced as per example 13, method E of WO 2013/076168. After addition of the remaining water-ethanol mixture the suspension formed was slowly cooled to 20° C. (at a rate of 10 K/h). Added to this suspension over 60 minutes at 20° C. were 21.56 g of isopropyl acetate. The mixture was stirred at 20° C. for a further 60 min before the solid was separated off, washed and dried under reduced pressure. This afforded methyl {4,6-diamino-2-[5-fluoro-1-(2-fluorobenzyl)-1H-pyrazolo [3,4-b]pyridin-3-yl]pyrimidin-5-yl}carbamate of formula (I) in the crystalline form of modification I in the form of the inventive active compound product.

Yield: 6.98 g (78.9% o. t.)

Example 3

8.86 g of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I, produced as per example 13, method E of WO 2013/076168 were heated to 75° C. in 35.8 g of DMSO. Added to the resulting clear solution over 360 min were 125.6 g of water (RT). Once the first 0.5 g of water had been added the solution was seeded with 59 mg of crystalline methyl {4,6-diamino-2-[5-fluoro-1-(2-fluorobenzyl)-1H-pyrazolo[3,4-b]pyridin-3-yl]pyrimidin-5-yl}carbamate in the crystalline form of modification I, produced as per example 13, method E of WO 2013/076168. After addition of the 125.6 g of water the suspension formed was slowly cooled to 20° C. (at a rate of 10 K/h). Added to this suspension over 60 minutes at 20° C. were 8.91 g of isopropyl acetate. The mixture was stirred at 20° C. for a further 60 min before the solid was separated off, washed and dried under reduced pressure. This afforded methyl {4,6-diamino-2-[5-fluoro-1-(2-fluorobenzyl)-1H-pyrazolo [3,4-b]pyridin-3-yl]pyrimidin-5-yl}carbamate of formula (I) in the crystalline form of modification I in the form of the inventive active compound product.

Yield: 6.36 g (71.8% o. t.)

Example 4

10.0 g of methyl {4,6-diamino-2-[5-fluoro-1-(2-fluorobenzyl)-1H-pyrazolo[3,4-b]pyridin-3-yl]pyrimidin-5-yl}carbamate of formula (I) as a di-DMSO solvate (71.4% w/w compound of formula (I), 28.6% w/w DMSO, produced as per example 13, method A up to the step "hot filtration of the suspension and washing with ethyl acetate" of WO 2013/076168) were suspended in 59.4 g of DMSO and heated to 75° C. 25.0 g of ethanol were added to the resulting clear solution and the mixture was stirred at 75° C. for 15 min. The solution was filtered and washed with 35.6 g of DMSO. The filtrate was heated to 75° C. and 84.9 g of water were added dropwise over 5 min. The suspension was cooled to 20° C. at a rate of 28 K/h and 41.0 g of isopropyl acetate were added over 60 min. The mixture was stirred at 20° C. for a further 30 minutes and the solid was isolated. This was then washed initially with 39.7 g of ethanol and subsequently with 39.6 g of isopropyl acetate. The moist product was dried overnight at 50° C. under reduced pressure with a nitrogen stream. This afforded methyl {4,6-diamino-2-[5-fluoro-1-(2-fluorobenzyl)-1H-pyrazolo[3,4-b] pyridin-3-yl]pyrimidin-5-yl}carbamate of formula (I) in the crystalline form of modification I in the form of the inventive active compound product.

Yield: 6.85 g (95.9% o. t.)

MS (ESIpos): m/z=427 (M+H)+

1H-NMR (400 MHz, DMSO-d6): δ=3.62 (br s, 3H), 5.79 (s, 2H), 6.22 (br s, 4H), 7.10-7.19 (m, 2H), 7.19-7.26 (m, 1H), 7.32-7.40 (m, 1H), 7.67 and 7.99 (2 br s, 1H), 8.66 (m, 1H), 8.89 (dd, 1H) ppm.

Example 5

20.0 g of methyl {4,6-diamino-2-[5-fluoro-1-(2-fluorobenzyl)-1H-pyrazolo[3,4-b]pyridin-3-yl]pyrimidin-5-yl}carbamate of formula (I) as a di-DMSO solvate (71.4% w/w compound of formula (I), 28.6% w/w DMSO, produced as per example 13, method A up to the step "hot filtration of the suspension and washing with ethyl acetate" of WO 2013/076168) were suspended in 100 g of DMSO and heated to 72° C. The resulting clear solution was added to a solution of 64.8 g of ethanol and 259.3 g of water temperature-controlled to 65° C. over 50 min. The suspension was cooled to 20° C. at a rate of 45 K/h and 75.0 g of isopropyl acetate were added over 50 min. The mixture was stirred at 20° C. for a further 19 hours and the solid was isolated. This was then washed with 120.0 g of ethanol. The moist product was dried overnight at 50° C. under reduced pressure with a nitrogen stream. This afforded methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I in the form of the inventive active compound product.

Yield: 13.6 g (93.2% o. t.)

Example 6

70.0 g of methyl {4,6-diamino-2-[5-fluoro-1-(2-fluorobenzyl)-1H-pyrazolo[3,4-b]pyridin-3-yl]pyrimidin-5-yl}carbamate of formula (I) as a di-DMSO solvate (71.4% w/w compound of formula (I), 28.6% w/w DMSO, produced as per example 13, method A up to the step "hot filtration of the suspension and washing with ethyl acetate" of WO 2013/076168) were suspended in 250 g of DMSO and heated to 72° C. The resulting clear solution was added to a solution of 251.8 g of ethanol and 982.6 g of water temperature-controlled to 65° C. over 50 min. The suspension was cooled to 20° C. at a rate of 45 K/h and 262.5 g of isopropyl acetate were added over 60 min. The mixture was stirred at 20° C. for a further 19 hours and the solid was isolated. This was then washed with 120.0 g of ethanol. The moist product was dried overnight at 50° C. under reduced pressure with a nitrogen stream. This afforded methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I in the form of the inventive active compound product.

Yield: 48.1 g (96.2% o. t.)

Example 7

Analysis by scanning electron microscopy: The powder samples for the analyses by scanning electron microscopy are prepared in a fume cupboard. To this end the samples should be filled into 5 mL (or smaller) rolled edge vials and the fill amount should be about 50 mg (approx. one spatula tip). To prepare the powder the SEM sample plate is provided with a conductive, double-sided adhesive carbon pad and adhesively bonded to the rolled edge of the vial. The vial containing the powder is turned upside down and the powder in the vial interior is scattered onto the adhesive surface of the sample holder. The powder is now adhesively bonded to the conductive adherent surface. The vial is turned upright again and nonadherent material is tapped off. The method is carried out without the use of a spatula and effectively in a closed system. The loaded sample plates are sputter-coated with a gold layer of 15-20 nm in thickness to produce a sufficient electrical conductivity. Imaging is carried out using a FEI ESEM Quanta 400 scanning electron microscope in the topography contrast mode using the secondary electrons emitted as a result of the interaction with the atoms of the sample surface. The images are captured at magnifications of 30×, 100×, 500×, 2000× and 5000×. An example at 30× magnification is shown for each production route of the active compound product (FIG. 1: route 1, FIG. 2: route 2).

Example 8

Figure 3:
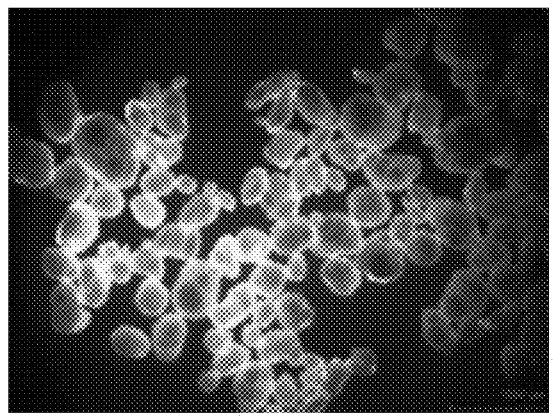
Figure 4:
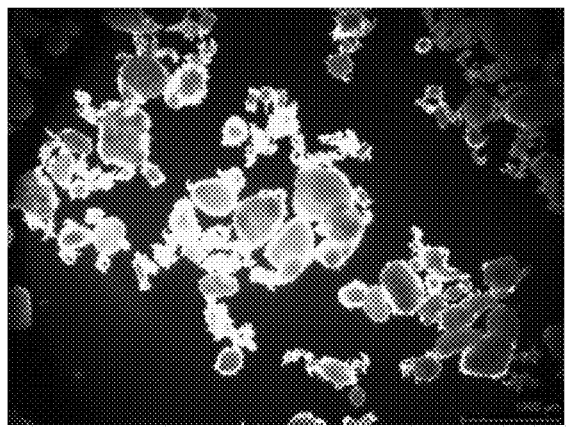
Figure 5:
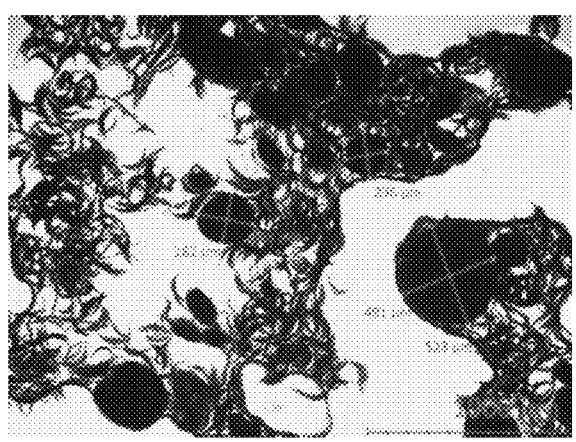

Active compound product of the compound of formula (I) produced according to example 2, 3, or 4 was analysed by polarization microscopy. The polarization microscopy analyses were performed using a Zeiss Axiolab instrument with an electronic image capture (DHS MicroCam 2022). Data processing was performed using BHS Bilddatenbank software (dhs Dietermann & Heuser Solution GmbH). For sample preparation, a small amount of the end suspension to be analysed was applied to a slide and carefully covered with a thin coverslip. FIGS. 3, 4 and 5 show polarization microscopy images of active compound product produced according to examples 2, 3 and 4 respectively.

Example 9

Determination of particle size distribution. Determination of particle size distribution is performed using a Sympatec Helos instrument fitted with a wet dispersion unit. To produce the dispersion medium 10-25 mg of the active compound product of the compound of formula (I) (micronized or non-micronized) are predispersed with 10 ml of water/1 drop of Tween 20 in a small vessel. The dispersion is stirred but not shaken to avoid foam formation. The dispersed material is subsequently added to the deionized water (approx. 0.5l) in the wet dispersion unit, treated with ultrasound for 5 minutes and measured (10 seconds). The sound exposure time is 5 minutes, a 50 mm aperture is employed (R2, or if measurement range exceeded, R3), the optical density of the suspension is 10-25%, the stirring/pumping speed is set to 50% (40-60%) and evaluation is carried out after 5 minutes of ultrasound.

The results of the measurements are shown in table 1. The three columns $X_{10\%}$, $X_{50\%}$ and $X_{90\%}$ indicate the diameter below which 10%, 50% and 90% respectively of the particles of the analysed active compound product lie. A comparable particle size spectrum can be obtained with active compound from both routes.

TABLE 1

Particle size distribution of various batches produced by route 1 and route 2

| Route | Batch | $X_{10\%}$ | $X_{50\%}$ | $X_{90\%}$ | Processing | Formulation example from table 3 |
|---|---|---|---|---|---|---|
| 1 | 2-1 | 1.0 μm | 11.1 μm | 43.0 μm | non-micronized | 4-1 (a) |
|  | 2-2 | 0.9 μm | 4.2 μm | 31.9 μm | non-micronized | 4-1 (b) |
|  | 2-3 | 1.0 μm | 4.3 μm | 27.4 μm | sieved | 4-1 (c) |
|  | 2-4 | 0.5 μm | 1.8 μm | 9.5 μm | micronized | 4-1 (d) |
| 2 | 2-5 | 1.4 μm | 18.7 μm | 50.6 μm | non-micronized | 4-1 (e) |

TABLE 1-continued

Particle size distribution of various batches produced by route 1 and route 2

| Route | Batch | $X_{10\%}$ | $X_{50\%}$ | $X_{90\%}$ | Processing | Formulation example from table 3 |
|---|---|---|---|---|---|---|
| | 2-6 | 1.0 μm | 9.0 μm | 34.4 μm | sieved | 4-1 (f) |
| | 2-7 | 0.6 μm | 4.1 μm | 23.6 μm | mixture sieved/ micronized | 4-1 (g) |
| | 2-8 | 0.6 μm | 2.6 μm | 13.6 μm | micronized | 4-1 (h) |

Example 10

Production of granulating suspension using micronized active compound. The granulating suspension is used for increasing the particle size of the employed initial charge through the binder present therein and for uniformly distributing the active compound in the resulting granulate. The composition of the solid dosage form is independent of whether micronized active compound from route 1 or micronized active compound from route 2 is employed. However, production of the granulating suspension is different. Incorporation of the active compound produced by route 2 does require slightly more water, thus insignificantly prolonging spray times during granulation. On the other hand the incorporation time required to introduce the active compound into the granulating suspension before homogenization thereof is significantly shortened. Altogether, this results in a process which is expedited and more manageable compared to the process according to route 1.

TABLE 2

Production of granulating suspension using micronized active compound produced by route 1 and route 2

| Example: Laboratory scale | Active compound from Route 1 | Active compound from Route 2 |
|---|---|---|
| Incorporation of the active compound into the granulating suspension [min] | 12-15 | 5-8 |
| Homogenizing of granulating suspension [min] | 10-15 | 10-15 |

Example 11

Production of solid dosage forms using various granulation processes.

Example 11.1: Fluidized Bed Granulation

Examples 4-1(a) to 4-1(h)

Initial charge process. Composition according to example 12, table 3. The binder and the wetting agent are dissolved in water. In the course of a fluidized bed granulation this binder solution is sprayed as granulation liquid onto the initial charge consisting of active compound, fillers and 50% of the disintegration promoter (disintegrant). After drying and sieving (mesh size 0.8 mm) of the resulting granulate the other 50% of the disintegration promoter and a lubricant are added and mixed. The resulting pressable mixture is pressed to afford solid dosage forms.

Examples 4-1(i) to 4-1(q)

Suspension process: Composition according to example 12, table 4. The binder and the wetting agent are dissolved in water and the active compound is suspended in this solution. In the course of a fluidized bed granulation this suspension is sprayed as granulation liquid onto the initial charge consisting of fillers and 50% of the disintegration promoter (disintegrant). After drying and sieving (mesh size 0.8 mm) of the resulting granulate the other 50% of the disintegration promoter and a lubricant are added and mixed. The resulting pressable mixture is pressed to afford solid dosage forms. The subsequent coating of the tablet is carried out with pigments suspended in an aqueous solution consisting of coating and film-forming agents and antiadhesive agents.

Example 11.2: Rapid Mixer Granulation

Examples 4-2(a) to 4-2(f)

Composition according to example 12, table 5. In a rapid mixer, active compound, fillers and 50% of the disintegration promoter (disintegrant) are mixed (granulate initial charge). An approx. 7.5% binder solution consisting of water, binder and wetting agent is produced and added as granulating liquid to the granulate initial charge. The whole mixture is uniformly mixed using a rapidly-rotating stirring means. Once mixing is complete the moist granulate is sieved (mesh size 2 mm) and dried. After sieving the dried granulate (mesh size 0.8 mm) said granulate is then admixed with 50% of the disintegration promoter and lubricant which is carried out in two separate mixing steps. The resulting pressable mixture is pressed to afford solid dosage forms.

Example 11.3: Dry Compaction

Examples 4-3(a) to 4-3(f)

Composition according to example 12, table 6. Active compound, filler, 50% of the disintegrant (disintegrants) and dry binder are mixed in a free-fall mixer. The powder mixture is sieved (mesh size 0.8 mm) and briquetted in an eccentric press using a 26 mm round ram. The briquettes are subsequently comminuted by hand and the obtained mixture is again passed through a 0.8 mm sieve. Sieved highdispersity silicon dioxide and the further 50% of sieved disintegrant (mesh size 0.5 mm in each case) were added and homogeneously distributed by mixing. The sieved lubricant was added prior to the last mixing step. The resulting pressable mixture is then pressed to afford solid dosage forms.

Example 11.4: Wet Dispersion

Examples 5-1; 5-2; 5-3; 5-4; 5-5; 5-6; 5-7

Composition according to example 12, table 7. The HPM-Cellulose 5 cP is incorporated into water by stirring. Subsequently added and incorporated by stirring are the sodium dodecyl sulfate and the active compound. Two different dispersing methods were used for the subsequent dispersing:

a) Examples 5-1 and 5-6

Use of an Ultra-Turrax IKA T25 fitted with an S25 N dispersing tool: In the jacket-cooled vessel the abovementioned mixture was dispersed at maximum speed (24 000 rpm) for between 40 and 45 min using the immersed Ultra-Turrax instrument.

b) Examples 5-2; 5-3; 5-4; 5-5; 5-7

Use of an IKA magicLAB laboratory colloid mill fitted with an MK dispersing tool: In the jacket-cooled vessel the abovementioned mixture was dispersed at the minimum slot width and at speeds between 14 600 and 23 000 rpm for between 25 and 40 min in recirculating mode.

In the course of a fluidized bed granulation the active compound suspension thus produced is sprayed as granulation liquid onto the initial charge consisting of fillers and 50% of the disintegration promoter (disintegrant). After drying and sieving (mesh size 0.8 mm) of the resulting granulate the other 50% of the disintegration promoter and a lubricant are added and mixed. The resulting pressable mixture is pressed to afford solid dosage forms.

Result:

Active compound product (I) produced by route 1: Using the fluidized bed process, rapid mixer granulation or wet dispersion results in rapid-release solid dosage forms which fulfill the release criterion (defined according to 6th release method) while using dry compaction results in solid dosage forms which do not fulfill the release criterion.

Active compound product (I) produced by route 2: Rapid-release solid dosage forms which fulfill the release criterion are obtained irrespective of the granulation process employed.

Active compound product (I) produced by route 2 thus offers broader applicability for all of the abovementioned granulation processes.

Example 12

TABLE 3

| Compositions of solid dosage form in mg/tablet | | |
|---|---|---|
| Ex. | 4-1(a) to 4-1(d) | 4-1(e) to 4-1(h) |
| Active compound product (I), route 1, non-micronized or sieved or micronized* | 10.0 | — |
| Active compound product (I), route 2, non-micronized or sieved or micronized* | — | 10.0 |
| Binder | | |
| HPMC 5cP | | 8.4 |
| sodium lauryl sulfate | | 1.2 |
| Filler | | |
| Microcrystalline cellulose | | 84.0 |
| Lactose monohydrate | | 117.0 |
| Disintegrant | | |
| Sodium croscarmellose | | 17.0 |
| Lubricant | | |
| Magnesium stearate | | 2.4 |
| Total | | 240.0 |
| Format (mm) | | r., 9WR15 |

*The active compound batches recited in example 9, table 1 having the specified particle size distributions were employed for manufacture.

TABLE 4

| Compositions in mg/solid dosage form | | | | | | | | | |
|---|---|---|---|---|---|---|---|---|---|
| Ex. | 4-1(i) | 4-1(j) | 4-1(k) | 4-1(l) | 4-1(m) | 4-1(n) | 4-1(o) | 4-1(p) | 4-1(q) |
| Active compound product (I), route 1, micron. | 1.25 | 2.5 | 5.0 | 10.0 | — | — | — | — | — |
| Active compound product (I), route 2, micron. | — | — | — | — | 2.5 | 5.0 | 10.0 | 15.0 | 15.0 |
| Binder | | | | | | | | | |
| HPMC 5cP | 4.24 | 4.20 | 4.24 | 8.40 | 4.20 | 4.24 | 8.40 | — | 12.60 |
| HPMC 3cP | — | — | — | — | — | — | — | 8.50 | — |
| Wetting agent | | | | | | | | | |
| Sodium lauryl sulfate | 0.28 | 0.40 | 0.56 | 1.20 | 0.40 | 0.56 | 1.20 | — | 1.80 |
| Polysorbate 20 | — | — | — | — | — | — | — | 3.35 | — |
| Filler | | | | | | | | | |
| Microcrystall. cellulose | 42.0 | 42.0 | 42.0 | 84.0 | 42.0 | 42.0 | 84.0 | 80.0 | 126.0 |
| Lactose monohydrate | 62.55 | 61.20 | 58.52 | 117.0 | 61.20 | 58.52 | 117.0 | 110.65 | 175.5 |
| Disintegrant | | | | | | | | | |
| Sodium croscarmellose | 8.48 | 8.50 | 8.48 | 17.00 | 8.50 | 8.48 | 17.00 | 20.0 | 25.50 |
| Lubricant | | | | | | | | | |
| Magnesium stearate | 1.20 | 1.20 | 1.20 | 2.40 | 1.20 | 1.20 | 2.40 | 2.50 | 3.60 |

TABLE 4-continued

| | | | | Compositions in mg/solid dosage form | | | | | |
|---|---|---|---|---|---|---|---|---|---|
| Ex. | 4-1(i) | 4-1(j) | 4-1(k) | 4-1(l) | 4-1(m) | 4-1(n) | 4-1(o) | 4-1(p) | 4-1(q) |
| | | | | Film coating | | | | | |
| HPMC 5cP | 2.0224 | 2.0224 | 2.0224 | 3.0336 | 2.00 | 2.00 | 3.00 | 3.0336 | 4.5504 |
| Talc | 0.4048 | 0.4048 | 0.4048 | 0.6072 | 0.40 | 0.40 | 0.60 | 0.6072 | 0.9108 |
| Red iron oxide | 0.0064 | 0.0064 | 0.0064 | 0.0096 | — | 0.35 | — | 0.0096 | 0.0144 |
| Yellow iron oxide | — | — | — | — | — | — | 0.825 | — | — |
| Titanium dioxide | 1.5664 | 1.5664 | 1.5664 | 2.3496 | 1.60 | 1.25 | 1.575 | 2.3496 | 3.5244 |
| Total | 124.0 | 124.0 | 124.0 | 246.0 | 124.0 | 124.0 | 246.0 | 246.0 | 369.0 |
| Format (mm) | | r., 7WR10 | | r., 9WR15 | r., 7WR10 | | r., 9WR15 | | o., 14x7WR6+2 |

TABLE 5

| | Compositions in mg/solid dosage form | | | | | |
|---|---|---|---|---|---|---|
| Ex. | 4-2(a) | 4-2(b) | 4-2(c) | 4-2(d) | 4-2(e) | 4-2(f) |
| Active compound product (I), route 1, micron. | 15.0 | 15.0 | 15.0 | — | — | — |
| Active compound product (I), route 2, micron. | — | — | — | 15.0 | 15.0 | 15.0 |
| Binder | | | | | | |
| HPMC 5cP | 8.5 | 4.25 | 12.75 | 8.5 | 4.25 | 12.75 |
| Wetting agent | | | | | | |
| Sodium lauryl sulfate | 2.00 | 2.00 | 2.00 | 2.00 | 2.00 | 2.00 |
| Filler | | | | | | |
| Microcrystalline cellulose | 80.0 | 40.0 | 120.0 | 80.0 | 40.0 | 120.0 |
| Lactose monohydrate | 112.0 | 47.5 | 176.5 | 112.0 | 47.5 | 176.5 |
| Disintegrant | | | | | | |
| Sodium croscarmellose | 20.00 | 10.00 | 30.00 | 20.00 | 10.00 | 30.00 |
| Lubricant | | | | | | |
| Magnesium stearate | 2.5 | 1.25 | 3.75 | 2.5 | 1.25 | 3.75 |
| Sum total | 240.0 | 120.0 | 360.0 | 240.0 | 120.0 | 360.0 |
| Format (mm) | r., 9WR15 | r., 7WR10 | r., 11WR18 | r., 9WR15 | r., 7WR10 | r., 11WR18 |

TABLE 6

| | Compositions in mg/solid dosage form | | | | | |
|---|---|---|---|---|---|---|
| | 4-3(a) | 4-3(b) | 4-3(c) | 4-3(d) | 4-3(e) | 4-3(f) |
| Active compound product (I), route 1, micron. | 15.0 | 15.0 | 15.0 | — | — | — |
| Active compound product (I), route 2, micron. | — | — | — | 15.0 | 15.0 | 15.0 |
| Filler | | | | | | |
| Microcrystalline cellulose | 199.25 | 91.125 | 187.25 | 199.25 | 91.125 | 187.25 |
| Dry binder | | | | | | |
| HPMC 5cP | — | — | 12.0 | — | — | — |
| HPMC SSL | — | — | — | — | — | 12.0 |
| Wetting agent | | | | | | |
| Sodium lauryl sulfate | 2.0 | 2.0 | 2.0 | 2.0 | 2.0 | 2.0 |

TABLE 6-continued

| | Compositions in mg/solid dosage form | | | | | |
|---|---|---|---|---|---|---|
| | 4-3(a) | 4-3(b) | 4-3(c) | 4-3(d) | 4-3(e) | 4-3(f) |
| Disintegrant | | | | | | |
| Sodium croscarmellose | 20.0 | 10.0 | 20.0 | 20.0 | 10.0 | 20.0 |
| Flow control agent | | | | | | |
| High-dispersity silicon dioxide | 1.25 | 0.625 | 1.25 | 1.25 | 0.625 | 1.25 |
| Lubricant | | | | | | |
| Magnesium stearate | 2.5 | 1.25 | 2.5 | 2.5 | 1.25 | 2.5 |
| Sum total | 240.0 | 120.0 | 240.0 | 240.0 | 120.0 | 240.0 |
| Format (mm) | r., 9WR15 | r., 7WR10 | r., 9WR15 | r., 9WR15 | r., 7WR10 | r., 9WR15 |

TABLE 7

| Compositions in mg/solid dosage form | | | | | | | |
|---|---|---|---|---|---|---|---|
| Ex. | 5-1 | 5-2 | 5-3 | 5-4 | 5-5 | 5-6 | 5-7 |
| Active compound product (I), route 1, non-micron. | | | 10.0 | | | | — |
| Active compound product (I), route 2, non-micron. | | | — | | | | 10.0 |
| Binder | | | | | | | |
| HPMC 5cP | | | 8.4 | | | | |
| Wetting agent | | | | | | | |
| Sodium lauryl sulfate | | | 1.2 | | | | |
| Filler | | | | | | | |
| Microcrystalline cellulose | | | 84.0 | | | | |
| Lactose monohydrate | | | 117.0 | | | | |
| Disintegrant | | | | | | | |
| Sodium croscarmellose | | | 17.0 | | | | |
| Lubricant | | | | | | | |
| Magnesium stearate | | | 2.4 | | | | |
| Sum total | | | 240.0 | | | | |
| Format (mm) | | | r., 9WR15 | | | | |

Example 13

Crushing strength. The crushing strength as a function of the various formats is comparable irrespective of the production process for the active compound. This is measured according to European Pharmacopoeia, 6th edition, main volume 2008.

Example 14

Release method. According to European Pharmacopoeia, 6th edition, main volume 2008, the drug form is tested with apparatus 2 (paddle). The rotation speed of the stirrer is 75 rpm (revolutions per minute) in 900 ml of 0.01N hydrochloric acid. The release criterion is then met if all 6 test specimens have released at least 80% of the active compound into the release medium after a test duration of 30 minutes. If 12 test specimens were tested the criteria apply analogously for all 12 test specimens.

TABLE 8

| Release results* and content after production of the solid dosage form (in %) | | | | | |
|---|---|---|---|---|---|
| Solid dosage form from ex. | 15 Min [%] | 30 Min [%] | 45 Min [%] | 60 Min [%] | Content [%] |
| 4-1 (a) | 61/72/66*) | 74/84/77 | 80/88/84 | 86/90/88 | 94.8 |
| 4-1 (b) | 64/65/64 | 75/76/75 | 80/81/80 | 83/85/84 | 99.6 |
| 4-1 (c) | 71/80/75 | 82/85/84 | 84/88/86 | 86/90/88 | 95.0 |
| 4-1 (d) | 88/95/92 | 97/98/98 | 98/98/98 | 98/99/98 | 98.7 |
| 4-1 (e) | 41/44/42 | 54/56/55 | 61/63/62 | 66/68/67 | 113.1 |
| 4-1 (f) | 38/40/39 | 53/58/55 | 62/68/65 | 68/75/71 | 98.3 |
| 4-1 (g) | 76/80/78 | 84/85/85 | 87/87/87 | 88/89/89 | 96.5 |
| 4-1 (h) | 83/89/86 | 90/93/91 | 92/93/93 | 93/93/93 | 93.1 |
| 4-1 (i) | 98/103/101 | 100/104/102 | 102/104/103 | 102/105/103 | 100.1 |
| 4-1 (j) | 93/98/95 | 95/99/97 | 96/99/97 | 96/99/97 | 97.9 |
| 4-1 (k) | 94/99/97 | 98/100/99 | 98/100/99 | 98/100/99 | 99.8 |
| 4-1 (l) | 84/94/91 | 97/101/98 | 98/102/100 | 98/102/100 | 100.0 |
| 4-1 (m) | 99/102/100 | 99/102/100 | 99/102/101 | 99/102/101 | 100.1 |
| 4-1 (n) | 87/97/91 | 97/98/98 | 97/99/98 | 97/99/98 | 98.6 |
| 4-1 (o) | 83/97/92 | 98/100/99 | 99/101/99 | 99/101/100 | 99.4 |
| 4-1 (p) | 96/99/98 | 97/100/98 | 99/101/100 | 99/101/100 | 100.6 |
| 4-1 (q) | 93/103/98 | 101/106/104 | 102/106/104 | 102/106/104 | 104.5 |
| 4-2 (a) | 87/89/88 | 95/97/96 | 97/99/98 | 98/100/99 | 103.1 |
| 4-2 (b) | 72/73/73 | 86/87/87 | 91/93/92 | 93/95/95 | 98.3 |
| 4-2 (c) | 80/85/83 | 86/91/90 | 89/93/92 | 90/94/93 | 97.5 |
| 4-2 (d) | 82/93/90 | 97/101/99 | 98/104/102 | 99/106/103 | 103.6 |
| 4-2 (e) | 70/79/73 | 86/93/88 | 92/98/94 | 95/101/97 | 100.6 |
| 4-2 (f) | 91/97/94 | 100/101/101 | 101/103/101 | 101/103/102 | 101.7 |
| 4-3 (a) | 63/68/66 | 71/76/74 | 75/80/78 | 77/83/80 | 99.2 |
| 4-3 (b) | 59/63/61 | 69/71/70 | 74/76/75 | 76/79/78 | 99.1 |
| 4-3 (c) | 55/67/57 | 62/68/66 | 67/72/70 | 70/76/73 | 96.9 |
| 4-3 (d) | 89/91/90 | 93/94/93 | 94/96/95 | 95/97/95 | 98.4 |
| 4-3 (e) | 84/85/85 | 91/92/92 | 93/94/93 | 94/95/94 | 98.0 |
| 4-3 (f) | 87/89/88 | 92/94/93 | 93/95/95 | 94/96/96 | 98.8 |
| 5-1 | 76/84/80 | 92/93/92 | 95/96/96 | 97/98/97 | 100.2 |
| 5-2 | 75/87/83 | 91/93/92 | 93/94/93 | 93/95/94 | 95.3 |
| 5-3 | 79/92/87 | 96/98/97 | 97/99/98 | 98/99/98 | 100.5 |
| 5-4 | 82/86/84 | 92/94/94 | 95/96/95 | 96/97/97 | 98.4 |
| 5-5 | 76/90/84 | 93/95/94 | 95/96/96 | 95/96/96 | 97.4 |
| 5-6 | 82/89/86 | 94/96/95 | 95/97/96 | 96/97/96 | 96.6 |
| 5-7 | 78/82/80 | 89/90/89 | 91/93/92 | 93/94/93 | 96.2 |

*)all values: min/max/average (n = 6 or n = 12)

Figure 6:
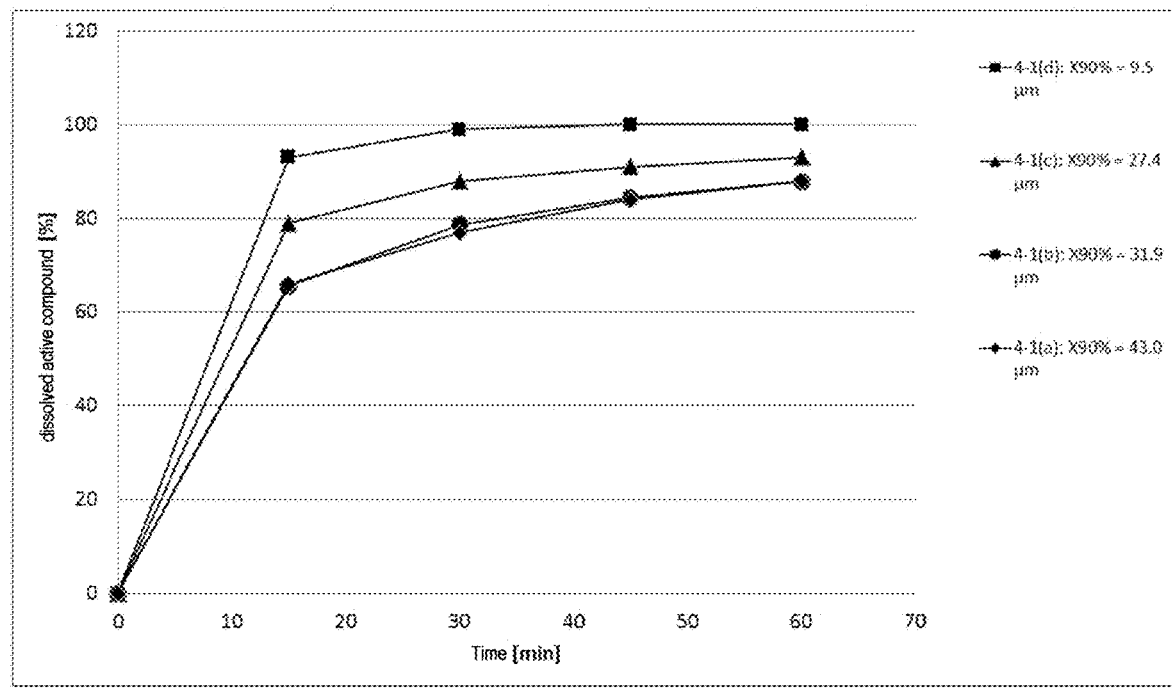

In the examples 4-1(a) to 4-1(h) the influence of active compound particle size on the release of the active compound from uncoated solid dosage forms was investigated. The active compound products specified in example 9 were incorporated into the solid dosage forms. The solid dosage forms were produced by fluidized bed granulation (example 11.1), the initial charge process being utilized in all examples. Active compound product of the compound of formula (I) produced by route 1 or route 2 was employed. Differences in release are shown in FIG. 6 for route 1 and in FIG. 7 for route 2.

When considering the active compound product of the compound of formula (I) produced by route 1, solid dosage forms containing the active compound product (I) with a particle size distribution having an $X_{90\%} \geq 30$ µm to $X_{90\%}=43$ µm do not meet the release criterion (method of example 14). The criterion is missed narrowly. In this particle size range differentiation of the release profiles is barely possible. By contrast, finer batches of the active compound product of the compound of formula (I) produced via route 1 and having an $X_{90\%}<10$ µm or $X_{90\%}=27$ µm do meet the release criterion.

When active compound product of the compound of formula (I) produced by route 2 is employed in the solid dosage forms, batches having an $X_{90\%}<14$ µm meet the release criterion. Active compound product (I) having a particle size distribution represented by an $X_{90\%}$ of 14 µm<X µm≤24 µm likewise meet the release criterion but release the active compound more slowly analogously to the results with active compound product of the compound of formula (I) produced by route 1. A clear difference is apparent in the release behaviour of the active compound product of the compound of formula (I) produced by route 2 in a particle size distribution having an $X_{90\%}>34$ µm. The solid dosage forms show a markedly slower release both compared to the previously considered batches and among one another compared to the specified particle size distributions ($X_{90\%}=34$ µm versus $X_{90\%}=51$ µm).

For the active compound product of the compound of formula (I) produced by route 2 it is therefore easier to differentiate via release kinetics between off-specification particle sizes and on-specification particle sizes. This specification is as follows: $X_{10\%} \geq 0.3$ µm, $X_{50\%}=1-8$ µm and $X_{90\%} \leq 201.1M$.

Examples 4-1(i) to 4-1(q) considered coated solid dosage forms likewise produced employing a fluidized bed granulation utilizing the suspension method. The coatings applied differ in the choice of colour pigments. Examples 4-1(i) bis 4-1(1) employed active compound product (I) produced by route 1 in micronized form while examples 4-1(m) to 4-1(q) incorporated active compound product (I) produced by route 2 in micronized form. All examples shown meet the release criterion defined according to example 14.

Examples 4-2(a) to 4-2(f) demonstrate the suitability of rapid mixer granulation as a further granulation process for producing granulates/solid dosage forms with active compound product (I) produced by route 1 or route 2. After production all compositions of the solid dosage forms meet the release criterion.

Examples 4-3(a) to 4-3(f) show differences in the suitability of dry compaction as a further granulation process for producing granulates/tablets with active compound product (I) produced by route 1 or route 2. While the use of active compound product (I) produced by route 1 results in solid dosage forms that do not meet the release criterion, the use of active compound product (I) produced by route 2 affords solid dosage forms that do meet the release criterion.

Examples 5-1 to 5-7 demonstrate the suitability of the wet dispersion process when using non-micronized active compound product (I) produced by route 1 or route 2 and thus the possibility of dispensing with a micronization of the active compound (I) before incorporation into the solid dosage forms while satisfying the release criterion from the solid dosage forms.

Example 15

Higher area-specific throughput in an inverting filter centrifuge. Industrial scale.

|  | Average area-specific throughput [kg/m²h] |
|---|---|
| Route 1 | 1.6 |
| Route 2 | 3.0 |

These data show an improved isolability of the material from route 2 compared to the material from route 1.

Example 16

Improved sieve throughput. Industrial scale.

|  | Sieve throughput of active compound product [kg/min] | Sieving machine |
|---|---|---|
| Route 1 | <10 kg of active compound product in 1 h i.e. < 0.17 kg/min | Frewitt Oscillowitt MG-800 (sieve aperture diameter 2.5 to 4.0 mm) |
| Route 2 | 65 kg of active compound product in < 5 min i.e. > 13 kg/min | Frewitt Coniwitt TC200 (sieve aperture diameter 3 mm) |

Observed here is a very large difference of a factor of nearly 100 in the sieve throughput of the active compound product of route 1 compared to the active compound product of route 2. This very large difference in the sieve throughput results predominantly from the material characteristics of the active compound product and cannot be explained by the different machine types.

Example 17

Figure 8:
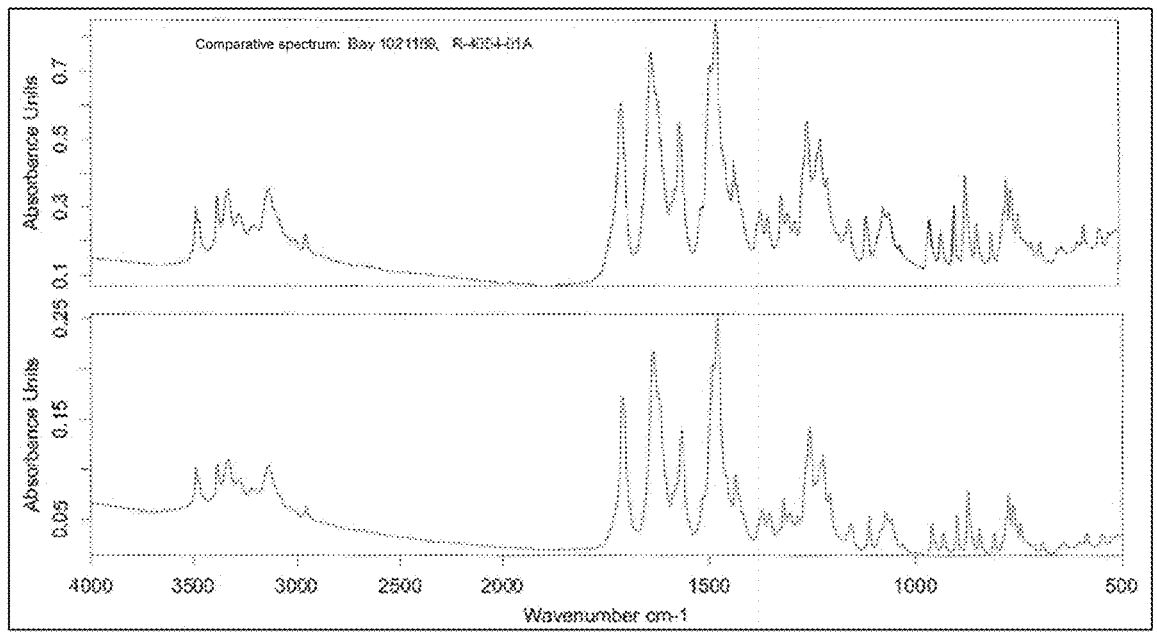

16.1 kg of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I, produced according to example 13, method E of WO 2013/076168, were micronized to afford 15.2 kg. The yield was 94.4%. FIG. 8 shows in the upper part an ATR IR diagram of a comparative batch of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I and in the lower part an ATR IR of the micronized compound. It was apparent that methyl {4,6-diamino-2-[5-fluoro-1-(2-fluorobenzyl)-1H-pyrazolo [3,4-b]pyridin-3-yl]pyrimidin-5-yl}carbamate of formula (I) remained in modification I even after micronization. The ATR IR diagram corresponds to the IR spectrum of the compound of formula (I) in modification I according to FIG. 1 of WO 2013/076168.

Example 18

39.0 kg of methyl {4,6-diamino-2-[5-fluoro-1-(2-fluorobenzyl)-1H-pyrazolo[3,4-b]pyridin-3-yl]pyrimidin-5-yl}carbamate of formula (I) in the crystalline form of modification I, produced by the process according to the invention of example 4, were micronized to afford 36.9 kg. The yield was 94.6%.

Figure 9:
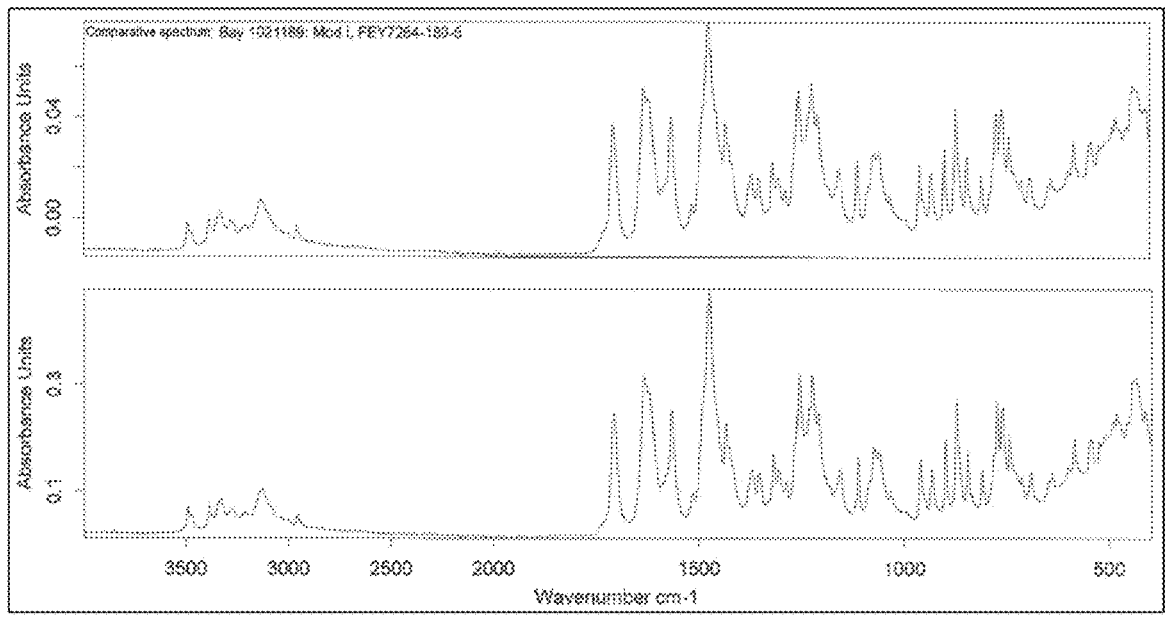

FIG. 9 shows in the upper part an ATR IR diagram of a comparative batch of methyl {4,6-diamino-2-[5-fluoro-1-(2-fluorobenzyl)-1H-pyrazolo[3,4-b]pyridin-3-yl]pyrimidin-5- yl}carbamate of formula (I) in the crystalline form of modification I and in the lower part an ATR IR of the micronized compound. It was apparent that methyl {4,6-diamino-2-[5-fluoro-1-(2-fluorobenzyl)-1H-pyrazolo[3,4-b]pyridin-3-yl]pyrimidin-5-yl}carbamate of formula (I), produced by the process according to the invention of example 4, remained in modification I even after micronization. The ATR IR diagram corresponds to the IR spectrum of the compound of formula (I) in modification I according to FIG. 1 of WO 2013/076168.

FIGURES

FIG. 1: Active compound product of the compound of formula (I), example 2-1, produced by the process according to WO 2013/076168 (route 1), analysis by scanning electron microscopy.

FIG. 2: Active compound product of the compound of formula (I), example 2-2, produced as per example 4 (route 2), analysis by scanning electron microscopy.

FIG. 3: Active compound product of the compound of formula (I), produced as per example 2 (route 2), analysis by polarization microscopy FIG. 4: Active compound product of the compound of formula (I), produced as per example 3 (route 2), analysis by polarization microscopy FIG. 5: Active compound product of the compound of formula (I), produced as per example 4 (route 2), analysis by polarization microscopy FIG. 6: Release kinetics of active compound product of different particle sizes produced by the process according to WO 2013/076168 (route 1)

Figure 7:
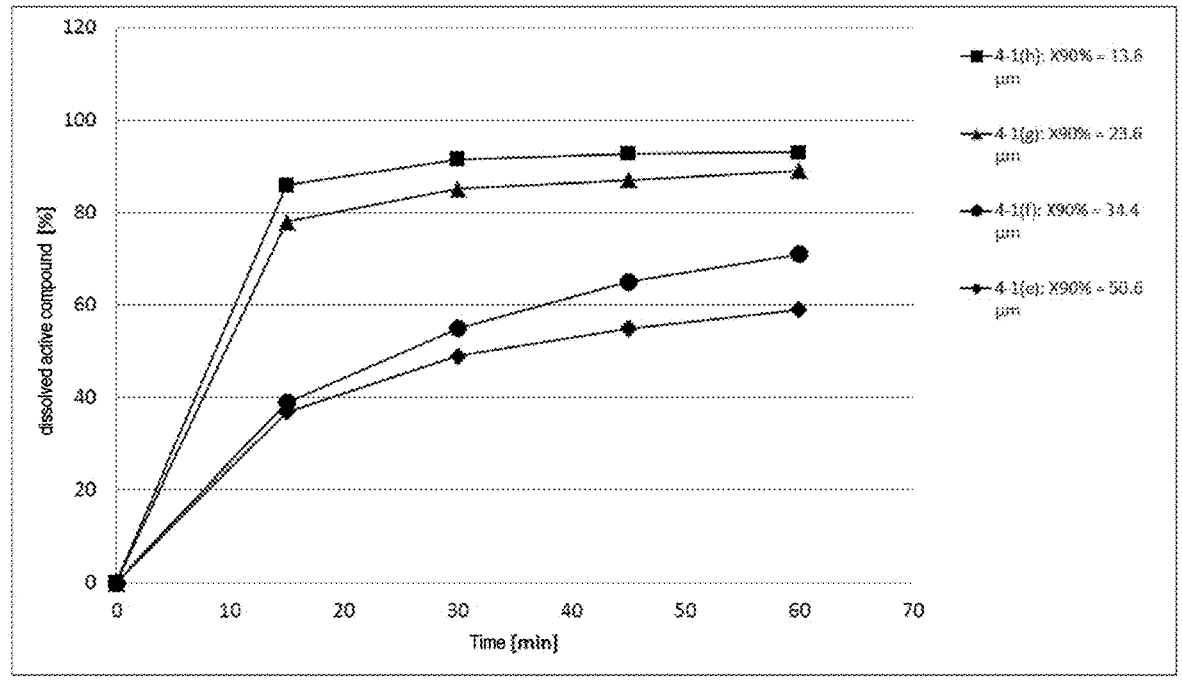

FIG. 7: Release kinetics of active compound product of different particle sizes produced as per example 4 (route 2)

FIG. 8: ATR IR diagram of the compound of formula (I) in the crystalline form of modification I, produced as per example 13, method E of WO 2013/076168, micronized FIG. 9: ATR IR diagram of the compound of formula (I) in the crystalline form of modification I, produced by the process according to the invention as per example 4, micronized

The invention claimed is:

1. A process for producing an active compound product of methyl {4,6-diamino-2-[5-fluoro-1-(2-fluorobenzyl)-1H-pyrazolo[3,4-b]pyridin-3-yl]pyrimidin-5-yl}carbamate of formula (I)

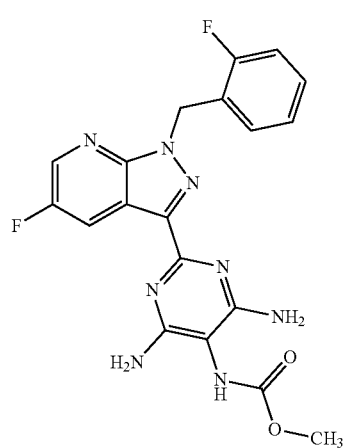

(I)

in the crystalline form of modification I, wherein the x-ray diffractogram of the compound of the formula (I) in modification I exhibits peak maxima of the 2 theta angle at 5.9, 6.9, 22.7, comprising:

a) dissolving the compound of formula (I) in solid form at a temperature of 30-100° C. in one or more polar and/or aprotic solvents or in one or more polar and/or aprotic solvents in combination with at least one wetting agent selected from the group consisting of methanol, ethanol, n-propanol, and isopropanol, b) subsequently crystallizing the dissolved compound of formula (I) out of the solution by adding water as antisolvent or of water in combination with at least one wetting agent selected from the group consisting of methanol, ethanol, n-propanol, and isopropanol, wherein the ratio of water to the at least one wetting agent added in step a) or b) is 1:0-20:1 w/w and the addition of water or of the combination of water with at least one wetting agent is carried out at a temperature of 30-100° C. and over a duration of 0.1 min-1200 min, or initially charging water as antisolvent or water in combination with at least one wetting agent and adding the compound of formula (I) dissolved according to step a), wherein the at least one wetting agent, the ratio of water to the at least one wetting agent added in step a) and/or b), the temperature and the duration over which the addition of the dissolved compound is carried out are as specified above;

c) subsequently cooling the suspension formed to a temperature of 5-50° C. at a cooling rate of 1-60 K/h; and d) subsequently agglomerating the crystals formed in step b) to afford active compound product by adding an agglomeration liquid, wherein in the case where a wetting agent was added in step a) and/or b) the ratio of the mass of the agglomeration liquid to the sum of the mass of the compound of formula (I) plus the mass of the at least one wetting agent added in step a) and/or b) is 0.3 to 2.0.

2. The process according to claim 1, wherein the at least one polar and/or aprotic solvent in step a) is selected from the group consisting of DMSO, N-methyl-2-pyrrolidone (NMP), dimethylacetamide (DMAc) and dimethylformamide (DMF) or combinations thereof with at least one wetting agent selected from the group consisting of methanol, ethanol, n-propanol, and isopropanol.

3. The process according to claim 1, wherein step a) employs DMSO as solvent in combination with ethanol as wetting agent, wherein the ratio between DMSO and ethanol is 1:0 to 5:1 w/w.

4. The process according to claim 1, further comprising following step a) by a filtration.

5. The process according to claim 1, wherein step b) comprises crystallizing the dissolved compound of formula (I) out of the solution by adding water as antisolvent or water in combination with at least one wetting agent selected from the group consisting of methanol, ethanol, n-propanol and isopropanol, wherein the ratio of water to the at least one wetting agent added in step a) or b) is 1:0-12:1 w/w and the addition of water or of the combination of water with at least one wetting agent is carried out at a temperature of 50-90° C. and over a period of 0.1 min-360 min, or initially charging water as antisolvent or water in combination with at least one wetting agent and adding the compound of formula (I) dissolved according to step a), wherein the at least one wetting agent, the ratio of water to the at least one wetting agent added in step a) and/or b), the temperature and the duration over which the addition of the dissolved compound is carried out are as specified above.

6. The process according to claim 1, wherein step c) comprises cooling the suspension formed to a temperature of 10-30° C. at a cooling rate of 5-45 K/h.

7. The process according to claim 1, wherein the agglomeration liquid employed in step d) is selected from the group consisting of methyl acetate, ethyl acetate, n-propyl acetate, isopropyl acetate, n-butyl acetate, and isobutyl acetate.

8. The process according to claim 1, further comprising step e) of isolating and drying the active compound product formed in step d), wherein step e) comprises washing the active compound product after isolation initially with a $C_1$-$C_4$ alcohol and subsequently with an acetate selected from methyl acetate, ethyl acetate, n-propyl acetate, isopropyl acetate, n-butyl acetate and isobutyl acetate and subsequently drying the active compound product under reduced pressure with a nitrogen stream at a temperature of 15-75° C.

9. The process according to claim 8, further comprising step f) of comminuting the active compound product after isolation and drying.

10. An active compound product of methyl {4,6-diamino-2-[5-fluoro-1-(2-fluorobenzyl)-1H-pyrazolo[3,4-b] pyridin-3-yl] pyrimidin-5-yl}carbamate of the compound of formula (I) in the crystalline form of modification I produced by the process according to claim 1.

11. The active compound product according to claim 10, wherein the active compound product has one or more of the following properties compared to the properties of a comparator active compound product of the compound of formula (I) in the crystalline form of modification I produced by the process of route 1, the properties selected from an elevated average area-specific throughput for isolation using a centrifuge with a batch size of >10 kg of active compound product, a higher maximum filtercake thickness at which the discharge path out of an inverting filter centrifuge does not become blocked, an elevated sieve throughput with a batch size of >10 kg of active compound product, and a shortened incorporation time required to introduce the active compound product into a granulating suspension before homogenization thereof, wherein the process of route 1 comprises the steps of preparing the compound of formula (I) from the di-dimethyl sulphoxide solvate thereof by stirring in ethyl acetate/ethanol at reflux, cooling, then filtering without (1) crystallizing a dissolved compound of formula (I) out of solution by contact with water as an antisolvent or water with a wetting agent, (2) subsequently cooling and (3) subsequently agglomerating crystals formed by adding an agglomeration liquid.

12. The active compound product produced by the process according to claim 8, wherein after the isolating and drying in step e) the active compound product contains no DMSO.

13. A solid dosage form containing active compound product of the compound of formula (I) produced by the process according to claim 1 and further containing microcrystalline cellulose, lactose monohydrate, hydroxypropylmethylcellulose 3 cP and/or 5 cP, sodium lauryl sulfate or polysorbate 20, sodium croscarmellose, magnesium stearate, talc, iron oxides and titanium dioxide.

* * * * *

UNITED STATES PATENT AND TRADEMARK OFFICE
CERTIFICATE OF CORRECTION

PATENT NO. : 12,172,996 B2
APPLICATION NO. : 17/414658
DATED : December 24, 2024
INVENTOR(S) : Fey et al.

It is certified that error appears in the above-identified patent and that said Letters Patent is hereby corrected as shown below:

In the Specification

In Column 2, Line 33, delete "didimethylsulfoxide" and insert -- di-dimethyl sulfoxide --, therefor.
In Column 2, Line 58, delete "didimethyl" and insert -- di-dimethyl sulfoxide --, therefor.
In Column 3, Line 2, delete "didimethyl" and insert -- di-dimethyl sulfoxide --, therefor.
In Column 4, Line 45, delete "abirateron" and insert -- abiraterone --, therefor.
In Column 4, Line 49, delete "abirateron" and insert -- abiraterone --, therefor.
In Column 5, Line 33, delete "agglomerization" and insert -- agglomeration --, therefor.
In Column 9, Line 33, delete "agglomerization" and insert -- agglomeration --, therefor.
In Column 13, Line 50, delete "didimethyl" and insert -- di-dimethyl sulfoxide --, therefor.
In Column 16, Line 18, delete "orb)" and insert -- or b) --, therefor.
In Column 16, Line 22, delete "orb)" and insert -- or b) --, therefor.
In Column 31, Line 35, delete "≤201.1M." and insert -- ≤20 µM. --, therefor.

In the Claims

In Column 36, Lines 14-15, in Claim 11, delete "didimethyl" and insert -- di-dimethyl sulfoxide --, therefor.

Signed and Sealed this
Twenty-fifth Day of March, 2025

Coke Morgan Stewart
*Acting Director of the United States Patent and Trademark Office*